(12) United States Patent
Bendele et al.

(10) Patent No.: US 6,306,820 B1
(45) Date of Patent: Oct. 23, 2001

(54) COMBINATION THERAPY USING A TNF BINDING PROTEIN FOR TREATING TNF-MEDIATED DISEASES

(75) Inventors: Alison M. Bendele, Nederland; Regina M. Sennello, Boulder, both of CO (US); Carl K. Edwards III, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/326,394

(22) Filed: Jun. 4, 1999

Related U.S. Application Data

(63) Continuation of application No. PCT/US97/22733, filed on Dec. 8, 1997.
(60) Provisional application No. 60/032,587, filed on Dec. 6, 1996, provisional application No. 60/036,355, filed on Jan. 23, 1997, provisional application No. 60/039,315, filed on Feb. 7, 1997, and provisional application No. 60/052,023, filed on Jul. 9, 1997.

(51) Int. Cl.$^7$ .................................................. A61K 38/17

(52) U.S. Cl. .............................................. 514/2; 530/350

(58) Field of Search ................................. 514/2; 530/350

(56) References Cited

U.S. PATENT DOCUMENTS

| | | |
|---|---|---|
| 4,179,337 | 12/1979 | Davis et al. . |
| 4,289,690 | 9/1981 | Pestka et al. . |
| 4,766,106 | 8/1988 | Katre et al. . |
| 4,847,325 | 7/1989 | Shadle et al. . |
| 4,917,888 | 4/1990 | Katre et al. . |
| 4,935,233 | 6/1990 | Bell et al. . |
| 4,959,314 | 9/1990 | Mark et al. . |
| 5,116,964 | 5/1992 | Capon et al. . |
| 5,122,614 | 6/1992 | Zalipsky . |
| 5,136,021 | 8/1992 | Dembinski et al. . |
| 5,153,265 | 10/1992 | Shadle et al. . |
| 5,166,322 | 11/1992 | Shaw et al. . |
| 5,211,945 | 5/1993 | Wallach et al. . |
| 5,252,714 | 10/1993 | Harris et al. . |
| 5,359,037 | 10/1994 | Wallach et al. . |
| 5,395,760 | 3/1995 | Smith et al. . |
| 5,446,090 | 8/1995 | Harris . |
| 5,478,925 | 12/1995 | Wallach et al. . |
| 5,512,544 | 4/1996 | Wallach et al. . |
| 5,605,690 | 2/1997 | Jacobs et al. . |
| 5,610,279 | 3/1997 | Brockhaus et al. . |
| 5,633,145 | 5/1997 | Feldmann et al. . |
| 5,695,953 | 12/1997 | Wallach et al. . |
| 5,712,155 | 1/1998 | Smith et al. . |
| 5,739,208 | 4/1998 | Harris . |
| 5,747,639 | 5/1998 | Seely . |
| 5,808,029 | 9/1998 | Brockhaus et al. . |
| 5,811,261 | 9/1998 | Wallach et al. . |
| 5,843,791 | 12/1998 | Hauptmann et al. . |
| 5,863,786 | 1/1999 | Feldmann et al. . |
| 6,096,728 * | 8/2000 | Collins et al. ................ 514/62 |

FOREIGN PATENT DOCUMENTS

| | | |
|---|---|---|
| 2003743 | 5/1990 | (CA) . |
| 0 259 863 A2 | 3/1988 | (EP) . |
| 0 308 378 A2 | 3/1989 | (EP) . |
| 0 334 165 A2 | 9/1989 | (EP) . |
| 0 398 327 A1 | 11/1990 | (EP) . |
| 0 412 486 A1 | 2/1991 | (EP) . |
| 0 418 014 A1 | 3/1991 | (EP) . |
| 0 422 339 A1 | 4/1991 | (EP) . |
| 0 433 900 A1 | 6/1991 | (EP) . |
| 0 512 528 A2 | 11/1992 | (EP) . |
| 0 526 905 A2 | 2/1993 | (EP) . |
| 2 218 101 A | 11/1989 | (GB) . |
| 2 246 569 A | 2/1992 | (GB) . |
| 90339 | 5/1989 | (IL) . |

(List continued on next page.)

OTHER PUBLICATIONS

Abuchowski et al., "Effect of Covalent Attachment of Polyethylene Glycol on Immunogenicity and Circulating Life of Bovine Liver Catalase", *Journal of Biological Chemistry*, 252(11):3582–3586 (1977).

Aggarwal, et al., "Characterization of Receptors for Human Tumour Necrosis Factor and Their Regulation by γ–Interferon", *Nature*, 318:665–667 (1985).

Akerblom et al., "Preparation and Characterization of Conjugates of Monoclonal Antibodies and Staphylococcal Enterotoxin A Using a New Hydrophilic Cross–Linker", *Bioconjugate Chem.*, 4:455–466 (1993).

Ashkenazi et al., "Protection Against Endotoxic Shock by a Tumor Necrosis Factor Receptor Immunoadhesin", *PNAS* 88:10535–10539 (1991).

Baglioni et al., "Binding of Human Tumor Necrosis Factor to High Affinity Receptors on HeLa and Lymphoblastoid Cells Sensitive to Growth Inhibition", *Journal of Biological Chemistry*, 260(25):13395–13397 (1985).

Barrera P. et al., "Circulating Soluble Tumor Necrosis Factor Receptors, Interleukin–2 Receptors, Tumor Necrosis Factor Alpha, and Interleukin–6 Levels in Rheumatoid Arthritis. Longitudinal Evaluation During Methotrexate and Azathioprine Therapy.", Arthritis & Rheumatism, 36(8): 1070–1079 (1993).

Bazzoni et al., "The Tumor Necrosis Factor Ligand and Receptor Families", *Seminars in Medicine of the Beth Israel Hospital,* Boston, 334(26):1717–1725 (1996).

(List continued on next page.)

Primary Examiner—Lorraine Spector
Assistant Examiner—Eileen B. O'Hara
(74) Attorney, Agent, or Firm—Thomas D. Zindrick; Steven M. Odre; Ron K. Levy

(57) ABSTRACT

The invention relates to methods for treating or preventing acute and/or septic shock. The method comprises administering to patients in need thereof therapeutically effective amounts of a TNF binding protein and a Fas antigen. In a preferred embodiment, the TNF binding protein is sTNFR-I or sTNFR-II. The invention also relates to pharmaceutical compositions containing a TNF binding protein and a Fas antigen useful in such methods.

8 Claims, 8 Drawing Sheets

FOREIGN PATENT DOCUMENTS

| | | |
|---|---|---|
| WO 90/12874 A2 | 11/1990 | (WO). |
| WO 90/13575 A1 | 11/1990 | (WO). |
| WO 91/03553 A1 | 3/1991 | (WO). |
| WO 92/01002 A1 | 1/1992 | (WO). |
| WO 92/01472 A1 | 2/1992 | (WO). |
| WO 92/07076 A1 | 4/1992 | (WO). |
| WO 92 07585 A | 5/1992 | (WO). |
| WO 92/13095 A1 | 8/1992 | (WO). |
| WO 92/16221 A1 | 10/1992 | (WO). |
| WO 93/01498 A1 | 1/1993 | (WO). |
| WO 94/06476 A1 | 3/1994 | (WO). |
| WO 95/13312 A1 | 5/1995 | (WO). |
| WO 95/34326 A1 | 12/1995 | (WO). |
| WO 96/20729 A | 7/1996 | (WO). |
| WO 98 05357 | 2/1998 | (WO). |

OTHER PUBLICATIONS

Beutler et al., "Passive Immunization against Cachectin/Tumor Necrosis Factor Protects Mice from Lethal Effect of Endotoxin", Science, 229:869–871 (1985).

Beutler and Cerami, "The Biology of Cachectin/TNF—A Primary Mediator of the Host Response", Ann. Rev. Immunol., 7:625–655 (1989).

Bologna, C. et al., "Association Des Traitements De Fond Dans La Polyarthrite Rheumatoid", Presse Medicale, 25(19):876–878 (1996) Abstract.

Borigini et al., "Combination Therapy", Bailliere S Clinical Rheumatology, 9(4):689–710 (1995).

Brockhaus et al., "Identification of Two Types of Tumor Necrosis Factor Receptors on Human Cell Lines by Monoclonal Antibodies," Proc. Natl. Acad. Sci. USA, 87:3127–3131 (1990).

Corcoran et al., "Characterization of Ligand Binding by the Human p55 Tumour–Necrosis–Factor Receptor Involvement of Individual Cysteine–Rich Repeats," Eur. J. Biochem., 223: 831–840 (1994).

Creasey et al., "A High Molecular Weight Component of the Human Tumor Necrosis Factor Receptor is Associated with Cytotoxicity," Proc. Natl. Acad. Sci. USA, 84:3293–3297 (1987).

Davis et al., "Soluble, Nonantigenic Polyethylene Glycol–Bound Enzymes", Biomedical Polymers: Polymeric Materials and Pharmaceuticals for Biomedical Use, Goldberg et al. (Ed.). published by Academic Press (NY), pp. 441–452 (1980).

Dayer et al., "Purification and Characterization of Human Tumor Necrosis Factor α Inhibitor," Chemical Abstracts, 113(38760n):454 (1990).

Dayer et al., "Interleukin–1, Tumor Necrosis Factor and Their Specific Inhibitors," European Cytokine Network, 5(6):563–571 (1994).

Elliott et al., "Randomised Double–blind Comparison of Chimeric Monoclonal Antibody to Tumour Necrosis Factor α (cA2) versus Placebo in Rheumatoid Arthritis", Lancet, 344:1105–1110 (1994).

Engelmann et al., "A Tumor Necrosis Factor–Binding Protein Purified to Homogeneity from Human Urine Protects Cells from Tumor Necrosis Factor Toxicity," J. Biol. Chem., 264(20):11974–11980 (1989).

Engelmann et al., "Antibodies to a Soluble Form of a Tumor Necrosis Factor (TNF) Receptor Have TNF–Like Activity", Journal of Biological Chemistry, 265(24):14497–14504 (1990).

Engelmann et al., "Two Tumor Necrosis Factor–Binding Proteins Purified From Human Urine," J. Biol. Chem., 265(3):1531–1536 (1990).

Feldman et al., "Receptor Activation by Antigens, Cytokines, Hormones, and Growth Factors" Annals of The New York Academy of Sciences, 766:272–278 (1995).

Fisher et al., "Treatment of Septic Shock with the Tumor Necrosis Factor Recptor:Fc Fusion Protein," The New England Journal of Medicine, 334(26): 1697–1702 (1996).

Gatanaga et al., "Purification and Characterization of an Inhibitor (Soluble Tumor Necrosis Factor Receptor) for Tumor Necrosis Factor and Lymphotoxin Obtained from the Serum Ultrafiltrates of Human Cancer Patients," Proc. National Academy of Science USA 87:8781–8784 (1990).

Goodwin et al., "Molecular Cloning and Expression of the Type 1 and Type 2 Murine Receptors for Tumor Necrosis Factor," Molecular and Cell Biology 11(6):3020–3026 (1991).

Gray et al., "Cloning of Human Tumor Necrosis Factor (TNF) Receptor cDNA and Expression of Recombinant soluble TNF–Binding Protein," Proc. Natl. Acad. Sci. USA, 87(19):7380–7384 (1990).

Hale et al., Cytokines and Their Receptors: From Clonal to Clinical Investigation—"Demonstration of In Vitro and In Vivo Efficacy of Two Biologically Active Human Soluble TNF Receptors Expressed in E. Coli," J. Cell. Biochem., Suppl. 15F:113 (1991).

Harris, Milton, "Laboratory Synthesis of Polyethylene Glycol Derivatives", Rev. Macromol. Chem. Phys., 25(3):325–373 (1985).

Harris et al., "Synthesis and Characterization of Poly(ethylene Glycol) Derivatives," Journal of Polymer Science-:Polymer Chemistry Edition, 22:341–352 (1984).

Hauser et al., "Cytokine Accumulations in CSF of Multiple Sclerosis Patients: Frequent Detection of Interleukin–1 and Tumor Necrosis Factor but not Interleukin–6," Neurology 40:1735–1739 (1990).

Heller et al., "Complementary DNA Cloning of a Receptor for Tumor Necrosis Factor and Demonstration of a Shed Form of the Receptor," Proc. Natl. Acad. Sci. USA, 87:6151–6155 (1990).

Himmler et al., "Molecular Cloning & Expression of Human & Rat Tumor Necrosis Factor Receptor Chain (p60) and Its Soluble Derivative, Tumor Necrosis Factor–Binding Protein," DNA and Cell Biology, 9(10):705–715 (1990).

Hofman et al., "Tumor Necrosis Factor Identified in Multiple Sclerosis Brain," J. Exp. Med. 170:607–612 (1989).

Hohmann et al., "Two Different Cell Types Have Different Major Receptors for Human Necrosis Factor (TNF α)," Journal of Biol. Chem. 264: 14927–14934 (1989).

Katz, Am. J. Med., "Modern Management of Rheumatoid Arthritis", The American Journal of Medicine, 79 (suppl 4C):24–31 (1985).

Kavanaugh et al., "Anti–TNG–Alpha Monoclonal Antibody (MAB) Treatment of Rheumatoid Arthritis (RA) Patients with Active Disease on Methotrexate (MTX); Results of a Double–Blind, Placebo Controlled Multicenter Trial", Arthritis & Rheumatism, 39(9):S123 (1996).

Kohno et al., "A Second Tumor Necrosis Factor Receptor Gene Product Can Shed a Naturally Occurring Tumor Necrosis Factor Inhibitor," Proc. Natl. Acad. Sci. USA, 87:8331–8335 (1990).

Krane and Simon, "Rheumatoid Arthritis: Clinical Features and Pathogenetic Mechanisms", Advances in Rheumatology, Synderman (ed.), 70(2):263–284 (1986).

Kull et al., "Cellular Receptor for $^{125}$I–Labeled Tumor Necrosis Factor: Specific Binding, Affinity Labeling, and Relationship to Sensitivity," Proc. Natl. Acad. Sci. USA, 82:5756–5760 (1985).

Lantz et al., "Characterization In Vitro of a Human Necrosis Factor–Binding Protein," J. Clin. Invest., 86:1396–1402 (1990).

Le et al., "Tumor Necrosis Factor and Interleukin 1: Cytokines with Multiple Overlapping Biological Activities," Lab Investigation 56(3):234–248 (1987).

Lehmann et al., "Demonstration of Membrane Receptors for Human Natural and Recombinant $^{125}$I–Labeled Tumor Necrosis Factor on HeLa Cell Clones and Their Role in Tumor Cell Sensitivity," Eur. J. Biochem. 158:1–5 (1986).

Lindvall et al., "Modulation of the Constitutive Gene Expression of the 55 KD Tumor Necrosis Factor Receptor in Hematopoietic Cells," Biochem. & Biophys. Res. Comm. 172(2)557–563 (1990).

Loetscher et al., "Molecular Cloning and Expression of the Human 55kd TNF Necrosis Factor Receptor," Cell, 61:351–359 (1990).

Loetscher et al., "Recombinant 55–kDa Tumor Necrosis Factor (TNF) Receptor," J. Biol. Chem. 266(27):18324–18329 (1991).

Marsters S. A. et al.: "Identification of Cystein–Rich Domains of the Type 1 Tumor Necrosis Factor Receptor Involved in Ligand Binding", The Journal of Biological Chemistry, 267(9): 5747–5750 (1992).

Moreland et al., "Treatment of Rheumatoid Arthritis with a Recombinant Human Tumor Necrosis Factor Receptor (p75)–Fc Fusion Protein", New England Journal of Medicine, 337:141–147 (1997).

Nophar et al., "Soluble forms of tumor necrosis factor receptors (TNF–Rs). The cDNA for the type I TNF–R, cloned using amino acid sequence data of its soluble form, encodes both the cell surface and a soluble form of the receptor," The EMBO J., 9(10):3269–3278 (1990).

Novick et al., "Soluble Cytokine Receptors are Present in Normal Human Urine," J. Exp. Med. 170:1409–1414 (1989).

Novick et al., "Soluble Cytokine Receptors are Present in Normal Human Urine," The Physiological and Pathological Effects of Cytokines, pp. 413–421 (1990).

Novick et al., "Purification of Soluble Cytokine Receptors from Normal Human Urine by Ligand–Affinity and Immunoaffinity Chromatography," J. Chromatog. 510:331–337 (1990).

Oliff et al., "Tumors Secreting Human TNF/Cachectin Induce Cachexia In Mice", Cell, 50:555–563; (1987).

Olsson et al., "Isolation and Characterization of a Tumor Necrosis Factor Binding Protein from Urine," Eur. J. Haematology, 42(3):270–275 (1989).

Opal et al., "Potential Hazards of Combination Immunotherapy in the Treatment of Experimental Septic Shock", The Journal of Infectious Diseases, 173:1415–1421 (1996).

Paleolog et al., "Deactivation Of Vascular Endothelium By Monoclonal Anti–Tumor Necrosis Factor α Antibody In Rheumatoid Arthritis," Arthritis & Rheumatism, 39:1082–1091 (1996).

Peetre et al., "A Tumor Necrosis Factor Binding Protein is Present in Human Biological Fluids," Eur. J. Haematology, 41:414–419 (1988).

Pennica et al., "Biochemical Properties of the 75–kDa Tumor Necrosis Factor Receptor", Journal of Biological Chemistry, 267(29):21172–21178 (1992).

Peppel et al., "A Tumor Necrosis Factor (TNF) Receptor–IgG Heavy Chain Chimeric Protein as a Bivalent Antagonist of TNF Activity," J. Exp. Med., 174:1483–1489 (1991).

Rankin et al., "The Therapeutic Effects of an Engineered Human Anti–Tumour Necrosis Factor Alpha Antibody (CDP571) in Rheumatoid Arthritis", British Journal of Rheumatology, 34:334–342, (1995).

Rhein, Reginald., "Another Sepsis Drug Down—Immunex' TNF Receptor," Biotechnology Newswatch, pp. 1–3 (Monday, Oct. 4, 1983).

Schall et al., "Molecular Cloning and Expression of a Receptor for Human Tumor Necrosis Factor," Cell, 61:361–370 (1990).

Scheurich et al., "Quantification and Characterization of a Tumor Necrosis Factor α (TNF–α) Inhibitor: Evidence of Immunological Cross–Reactivity with the TNF Receptor," Proc. Natl. Acad. Sci. USA, 87:5188–5192 (1990).

Seckinger et al., "Purification and Biologic Characterization of a Specific Tumor Necrosis Factor α Inhibitor," J. Biol. Chem., 264(20):11966–11973 (1989).

Seckinger et al., "A Urine Inhibitor of Interleukin 1 Activity That Blocks Ligand Binding." J. Immunol., 139(5):1546–1549 (1987).

Seely et al., "Manufacturing of Recombinant Tumor Necrosis Factor Binding Protein 'Dumbbell' Using a 20K PEG BIS–Vinylsulfone Linker," 209th Am. Chem. Soc. National Meeting, Anaheim, Cal., Apr. 2–6, 1995, BIOT 68.

Seitz et al., "Methotrexate in Rheumatoid Arthritis: Stimulation of Cytokine Inhibitor and Inhibition of Chemokine Production by Peripheral Blood Mononuclear Cells", British Journal of Rheumatology, 34(7):602–609 (1995).

Seitz et al., "Interleukin 1 (IL–1) Receptor Antagonist, Soluble Tumor Necrosis Factor Receptors, IL–1 beta, and IL–8–markers of Remission in Rheumatoid Arthritis During Treatment with Methotrexate", Journal of Rheumatology, 23(9):1512–1516 (1996).

Selby et al. "Endogenous Tumor Necrosis Factor in Cancer Patients", Lancet, 1(8583):483 (1988).

Silberberg, "Diseases of Joints", Anderson's Pathology, Kissane (ed.), II:1828–1836 (1985).

Smith, Craig, "cDNA Expression: Cloning of the Receptor for Human Tumor Necrosis Factor." Presentation Programme, 29th Midwinter Conference of Immunologists (Jan. 27–30, 1990).

Smith, Craig, "cDNA Expression: Cloning of the Receptor for Human Tumor Necrosis Factor." Presentation at the 29th Midwinter Conference of Immunologists (Jan. 27–30, 1990).

Smith et al., "A Receptor for Tumor Necrosis Factor Defines an Unusual Family of Cellular and Viral Proteins," *Science*, 248:1019–1023 (1990).

Smith et al., "A Receptor for Tumor Necrosis Factor Defines an Unusual Family of Cellular and Viral Proteins," Genbank database excerpt released after publication (May 1990).

Smith et al., "Species Specificity of Human and Murine Tumor Necrosis Factor," *J. Biol. Chem.*, 261(32):14871–14874 (1986).

Spinas et al., "Induction of Plasma Inhibitors of Interleukin 1 and TNF–Alpha Activity by Endotoxin Administration to Normal Humans," *Am. J. Physiol.* 259:R993–R997 (1990).

Starnes, Jr. et al., "Tumor Necrosis Factor and the Acute Metabolic Response to Tissue Injury in Man" 82:1321–1325 (1988).

Stauber et al., "Human Tumor Necrosis Factor–α Receptor," *J. Biol. Chem.*, 263(35):19098–19104 (1988).

Stauber et al., "Characterization and Affinity Cross–Linking of Receptors for Human Recombinant Lymphotoxin (Tumor Necrosis Factor–β) on a Human Histiocytic Lymphoma Cell Line U–937," *J. Biol. Chem.* 264(6):3573–3576 (1989).

Tak et al., "Decrease in Cellularity and Expression of Adhesion Molecules by Anti–Tumor Necrosis Factor α Monoclonal Antibody Treatment in Patients with Rheumatoid Arthritis," *Arthritis and Rheumatism*, 39:1077–1081 (1996).

Tracey et al., "Anti–Cachectin/TNF Monoclonal Antibodies Prevent Septic Shock During Lethal Bacteraemia," *Nature* 330:662–664 (1987).

Tracey et al., "Metabolic Effects of Cachectin/Tumor Necrosis Factor Are Modified by Site of Production," *J. Clin. Invest.* 86:2014–2024 (1990).

Tracey et al., "Physiological responses to cachectin," Tumor necrosis factor and related cytotoxins. Wiley, Chichester (Ciba Foundation Symposium 131), pp. 88–108 (1987).

Tsujimoto et al., "Characterization and Affinity Crosslinking of Receptors for Tumor Necrosis Factor on Human Cells," *Archives of Biochem. & Biophys.* 249(2):563–568 (1986).

Van Zee et al., "Tumor Necrosis Factor Soluble Receptors Circulate During Experimental and Clinical Inflammation and Can Protect Against Excessive Tumor Necrosis Factor α In Vitro and In Vivo", *Proc. Natl. Acad. Sci. USA*, 89:4845–4849 (1992).

Vilcek et al., "Tumor Necrosis Factor: Receptor Binding and Mitogenic Action in Fibroblasts", *Journal of Cellular Physiology Supplement* 5:57–61 (1987).

Vitt et al., "Biological and Structural Characterization of the Tumor Necrosis Factor Receptor on Multiple Cell Types: Relationship to Function", Fed. Proc. 78$^{th}$ Annual Meeting of the American Society of Biological Chemists 46 (6):2117 (Abstract 1118) (1987).

Waage et al., "Association Between Tumour Necrosis Factor in Serum and Fatal Outcome in Patients with Meningococcal Disease", *Lancet*, 1(8529):355 (1987).

Wallach et al., "Cell Surface and Soluble TNF Receptors", Tumor Necrosis Factor: Structure–Function Relationship and Clinical Application, Osawa T, Bonavida B (eds), Karger, Basel. 47–57 (1992).

Wallach et al., "Mechanisms Which Take Part in Regulation of the Response to Tumor Necrosis Factor," *Lymphokine Research* 8(3):359–363 (1989).

Wallach, David, "Preparations of Lymphotoxin Induce Resistance to Their Own Cytotoxic Effect," *J. Immunol.* 132(5):2464–2469 (1984).

Wallach et al., "Regulation of the Response to Tumor Necrosis Factor," Tumor Necrosis Factor/Cachectin and Related Cytokines Int. Conf., Heidelberg 1987, Tumor Necrosis Factor and Related Cytotoxins, Bonavida, Gifford, Kirchner, Old (eds), Karger, Basel. pp. 134–147 (1988).

Yoshie et al., "Binding and Crosslinking of $^{125}$I–Labeled Recombinant Human Tumor Necrosis Factor to Cell Surface Receptors," *J. Biochem.* 100:531–541 (1986).

* cited by examiner

FIG. 1

```
5'-GATAGTGTGTGTCCCCAAGGAAAATATATCCACCCTCAAAATAATTCGATTTGCTGTACC-
   +---------+---------+---------+---------+---------+---------+
    D  S  V  C  P  Q  G  K  Y  I  H  P  Q  N  N  S  I  C  C  T  -

-AAGTGCCACAAAGGAACCTACTTGTACAATGACTGTCCAGGCCCGGGGCAGGATACGGAC-
  +---------+---------+---------+---------+---------+---------+
     K  C  H  K  G  T  Y  L  Y  N  D  C  P  G  P  G  Q  D  T  D  -

-TGCAGGGAGTGTGAGAGCGGCTCCTTCACCGCTTCAGAAAACCACCTCAGACACTGCCTC-
  +---------+---------+---------+---------+---------+---------+
     C  R  E  C  E  S  G  S  F  T  A  S  E  N  H  L  R  H  C  L  -

-AGCTGCTCCAAATGCCGAAAGGAAATGGGTCAGGTGGAGATCTCTTCTTGCACAGTGGAC-
  +---------+---------+---------+---------+---------+---------+
     S  C  S  K  C  R  K  E  M  G  Q  V  E  I  S  S  C  T  V  D  -

-CGGGACACCGTGTGTGGCTGCAGGAAGAACCAGTACCGGCATTATTGGAGTGAAAACCTT-
  +---------+---------+---------+---------+---------+---------+
     R  D  T  V  C  G  C  R  K  N  Q  Y  R  H  Y  W  S  E  N  L  -

-TTCCAGTGCTTCAATTGCAGCCTCTGCCTCAATGGGACCGTGCACCTCTCCTGCCAGGAG-
  +---------+---------+---------+---------+---------+---------+
     F  Q  C  F  N  C  S  L  C  L  N  G  T  V  H  L  S  C  Q  E  -

-AAACAGAACACCGTGTGCACCTGCCATGCAGGTTTCTTTCTAAGAGAAAACGAGTGTGTC-
  +---------+---------+---------+---------+---------+---------+
     K  Q  N  T  V  C  T  C  H  A  G  F  F  L  R  E  N  E  C  V  -

-TCCTGTAGTAACTGTAAGAAAAGCCTGGAGTGCACGAAGTTGTGCCTACCCCAGATTGAG-
  +---------+---------+---------+---------+---------+---------+
     S  C  S  N  C  K  K  S  L  E  C  T  K  L  C  L  P  Q  I  E  -

-AAT-3'
  +-----
   N  *
```

FIG. 2

```
5'-TTGCCCGCCCAGGTGGCATTTACACCCTACGCCCCGGAGCCCGGGAGCACATGCCGGCTC-
   +---------+---------+---------+---------+---------+---------+
    L  P  A  Q  V  A  F  T  P  Y  A  P  E  P  G  S  T  C  R  L  -

-AGAGAATACTATGACCAGACAGCTCAGATGTGCTGCAGCAAGTGCTCGCCGGGCCAACAT-
 +---------+---------+---------+---------+---------+---------+
   R  E  Y  Y  D  Q  T  A  Q  M  C  C  S  K  C  S  P  G  Q  H  -

-GCAAAAGTCTTCTGTACCAAGACCTCGGACACCGTGTGTGACTCCTGTGAGGACAGCACA-
 +---------+---------+---------+---------+---------+---------+
   A  K  V  F  C  T  K  T  S  D  T  V  C  D  S  C  E  D  S  T  -

-TACACCCAGCTCTGGAACTGGGTTCCCGAGTGCTTGAGCTGTGGCTCCCGCTGTAGCTCT-
 +---------+---------+---------+---------+---------+---------+
   Y  T  Q  L  W  N  W  V  P  E  C  L  S  C  G  S  R  C  S  S  -

-GACCAGGTGGAAACTCAAGCCTGCACTCGGGAACAGAACCGCATCTGCACCTGCAGGCCC-
 +---------+---------+---------+---------+---------+---------+
   D  Q  V  E  T  Q  A  C  T  R  E  Q  N  R  I  C  T  C  R  P  -

-GGCTGGTACTGCGCGCTGAGCAAGCAGGAGGGGTGCCGGCTGTGCGCGCCGCTGCGCAAG-
 +---------+---------+---------+---------+---------+---------+
   G  W  Y  C  A  L  S  K  Q  E  G  C  R  L  C  A  P  L  R  K  -

-TGCCGCCCGGGCTTCGGCGTGGCCAGACCAGGAACTGAAACATCAGACGTGGTGTGCAAG-
 +---------+---------+---------+---------+---------+---------+
   C  R  P  G  F  G  V  A  R  P  G  T  E  T  S  D  V  V  C  K  -

-CCCTGTGCCCCGGGGACGTTCTCCAACACGACTTCATCCACGGATATTTGCAGGCCCCAC-
 +---------+---------+---------+---------+---------+---------+
   P  C  A  P  G  T  F  S  N  T  T  S  S  T  D  I  C  R  P  H  -

-CAGATCTGTAACGTGGTGGCCATCCCTGGGAATGCAAGCAGGGATGCAGTCTGCACGTCC-
 +---------+---------+---------+---------+---------+---------+
   Q  I  C  N  V  V  A  I  P  G  N  A  S  R  D  A  V  C  T  S  -

-ACGTCCCCCACCCGGAGTATGGCCCCAGGGGCAGTACACTTACCCCAGCCAGTGTCCACA-
 +---------+---------+---------+---------+---------+---------+
   T  S  P  T  R  S  M  A  P  G  A  V  H  L  P  Q  P  V  S  T  -

-CGATCCCAACACACGCAGCCAACTCCAGAACCCAGCACTGCTCCAAGCACCTCCTTCCTG-
 +---------+---------+---------+---------+---------+---------+
   R  S  Q  H  T  Q  P  T  P  E  P  S  T  A  P  S  T  F  L  -

-CTCCCAATGGGCCCCAGCCCCCCAGCTGAAGGGAGCACTGGCGAC-3'
 +---------+---------+---------+---------+----
   L  P  M  G  P  S  P  P  A  E  G  S  T  G  D  *
```

COMBINATION THERAPY USING A TNF BINDING PROTEIN FOR TREATING TNF-MEDIATED DISEASES

This application is a continuation of International Application No. PCT/US97/22733, filed Dec. 8, 1997, which claims the benefit of U.S. Provisional Application No. 60/032,587, filed Dec. 6, 1996, U.S. Provisional Application No. 60/036,355, filed Jan. 23, 1997, U.S. Provisional Application No. 60/039,315, filed Feb. 7, 1997 and U.S. Provisional Application No. 60/052,023, filed Jul. 9, 1997, all of which are hereby incorporated by reference herein.

FIELD OF THE INVENTION

The present invention relates to the field of TNF-mediated diseases. More specifically, the present invention relates to combination therapy for the purpose of preventing or treating TNF-mediated diseases.

BACKGROUND OF THE INVENTION

Inflammation is the body's defense reaction to injuries such as those caused by mechanical damage, infection or antigenic stimulation. An inflammatory reaction may be expressed pathologically when inflammation is induced by an inappropriate stimulus such as an autoantigen, is expressed in an exaggerated manner or persists well after the removal of the injurious agents. Such inflammatory reaction may include the production of certain cytokines.

While the etiology of inflammation is poorly understood, considerable information has recently been gained regarding the molecular aspects of inflammation. This research has led to identification of certain cytokines which are believed to figure prominently in the mediation of inflammation. Cytokines are extracellular proteins that modify the behavior of cells, particularly those cells that are in the immediate area of cytokine synthesis and release. Tumor necrosis factors (TNFs) are a class of cytokines produced by numerous cell types, including monocytes and macrophages.

At least two TNFs have been previously described, specifically TNF alpha (TNF-α) and TNF beta (TNF-β or lymphotoxin), and each is active as a trimeric molecule and is believed to initiate cellular signaling by crosslinking receptors (Engelmann et al. (1990), *J. Biol. Chem.*, 265:14497–14504).

Several lines of evidence implicate TNF-α and TNF-β as major inflammatory cytokines. These known TNFs have important physiological effects on a number of different target cells which are involved in inflammatory responses to a variety of stimuli such as infection and injury. The proteins cause both fibroblasts and synovial cells to secrete latent collagenase and prostaglandin $E_2$ and cause osteocyte cells to stimulate bone resorption. These proteins increase the surface adhesive properties of endothelial cells for neutrophils. They also cause endothelial cells to secrete coagulant activity and reduce their ability to lyse clots. In addition they redirect the activity of adipocytes away from the storage of lipids by inhibiting expression of the enzyme lipoprotein lipase. TNFs also cause hepatocytes to synthesize a class of proteins known as "acute phase reactants," which act on the hypothalamus as pyrogens (Selby et al. (1988), *Lancet*, 1 (8583):483; Starnes, Jr. et al. (1988), *J. Clin. Invest.*, 82:1321; Oliff et al. (1987), *Cell*, 50:555; and Waage et al. (1987), *Lancet*, 1 (8529):355).

A disease or medical condition is considered to be a "TNF-mediated disease" if the spontaneous or experimental disease is associated with elevated levels of TNF in bodily fluids or in tissues adjacent to the focus of the disease or indication within the body. TNF-mediated diseases may also be recognized by the following two conditions: (1) pathological findings associated with a disease can be mimicked experimentally in animals by the administration of TNF and (2) the pathology induced in experimental animal models of the disease can be inhibited or abolished by treatment with agents which inhibit the action of TNF. Many TNF-mediated diseases satisfy two of these three conditions, and others will satisfy all three conditions.

TNF-mediated diseases such as rheumatoid arthritis and psoriatic arthritis are chronic joint diseases that afflict and disable, to varying degrees, millions of people worldwide. Rheumatoid arthritis is a disease of articular joints in which the cartilage and bone are slowly eroded away by a proliferative, invasive connective tissue called pannus, which is derived from the synovial membrane. The disease may involve peri-articular structures such as bursae, tendon sheaths and tendons as well as extra-articular tissues such as the subcutis, cardiovascular system, lungs, spleen, lymph nodes, skeletal muscles, nervous system (central and peripheral) and eyes (Silberberg (1985), *Anderson's Pathology*, Kissane (ed.), II:1828).

It is believed that rheumatoid arthritis results from the presentation of a relevant antigen to an immunogenetically susceptible host. The antigens that could potentially initiate an immune response resulting in rheumatoid arthritis might be endogenous or exogenous. Possible endogenous antigens include collagen, mucopolysaccharides and rheumatoid factors. Exogenous antigens include mycoplasms, mycobacteria, spirochetes and viruses. By-products of the immune reaction inflame the synovium (i.e., prostaglandins and oxygen radicals) and trigger destructive joint changes (i.e., collagenase).

There is a wide spectrum of disease severity, but many patients run a course of intermittent relapses and remissions with an overall pattern of slowly progressive joint destruction and deformity. The clinical manifestations may include symmetrical polyarthritis of peripheral joints with pain, tenderness, swelling and loss of function of affected joints; morning stiffness; and loss of cartilage, erosion of bone matter and subluxation of joints after persistent inflammation. Extra-articular manifestations include rheumatoid nodules, rheumatoid vasculitis, pleuropulmonary inflammations, scleritis, sicca syndrome, Felty's syndrome (splenomegaly and neutropenia), osteoporosis and weight loss (Katz (1985), *Am. J. Med.*, 79:24 and Krane and Simon (1986), *Advances in Rheumatology*, Synderman (ed.), 70(2):263–284). The clinical manifestations result in a high degree of morbidity resulting in disturbed daily life of the patient.

Additionally, preclinical results with various predictive animal models of rheumatoid arthritis have suggested that inhibition of TNF-α can have a major impact on disease progression and severity (Dayer et al. (1994), *European Cytokine Network*, 5(6):563–571 and Feldmann et al. (1995), *Annals Of The New York Academy Of Sciences*, 66:272–278). Moreover, recent human clinical trials in rheumatoid arthritis with inhibitors of TNF have shown promising results (Rankin et al. (1995), *British Journal Of Rheumatology*, 3(4):4334–4342; Elliott et al. (1995), *Lancet*, 344:1105–1110; Tak et al. (1996), *Arthritis and Rheumatism*, 39:1077–1081; Paleolog et al. (1996), *Arthritis and Rheumatism*, 39:1082–1091 and Moreland et al. (1997), *New England Journal of Medicine*, 337:141–147.).

It is an object of the present invention to provide therapeutic methods and compositions for the treatment of TNF-mediated diseases. This and other objects of the present invention will become apparent from the description hereinafter.

SUMMARY OF THE INVENTION

The present invention relates to therapies for preventing and treating TNF-mediated diseases in a patient. The present invention specifically relates to combination therapy using a TNF binding protein for preventing and treating TNF-mediated diseases, including rheumatic diseases, and the systemic inflammation and body weight loss associated therewith. The type of treatment herein referred to is intended for mammals, including humans.

BRIEF DESCRIPTION OF THE FIGURES

Numerous aspects and advantages of the present invention will become apparent upon review of the figures, wherein:

FIG. 1 depicts a nucleic acid sequence (SEQ ID NO:1) encoding $Asp^1$-$Thr^{161}$, mature recombinant human soluble TNF receptor type I. Also depicted is the amino acid sequence (SEQ ID NO:2) of $Asp^1$-$Thr^{161}$. The amino terminus of the amino acid sequence may be methionylated or nonmethionylated.

FIG. 2 depicts a nucleic acid sequence (SEQ ID NO:3) encoding $Leu^1$-$Thr^{179}$, mature recombinant human soluble TNF receptor type II. Also depicted is the amino acid sequence (SEQ ID NO:4) of $Leu^1$-$Thr^{179}$. The amino terminus of the amino acid sequence may be methionylated or nonmethionylated.

DETAILED DESCRIPTION OF THE INVENTION

Figure 3:
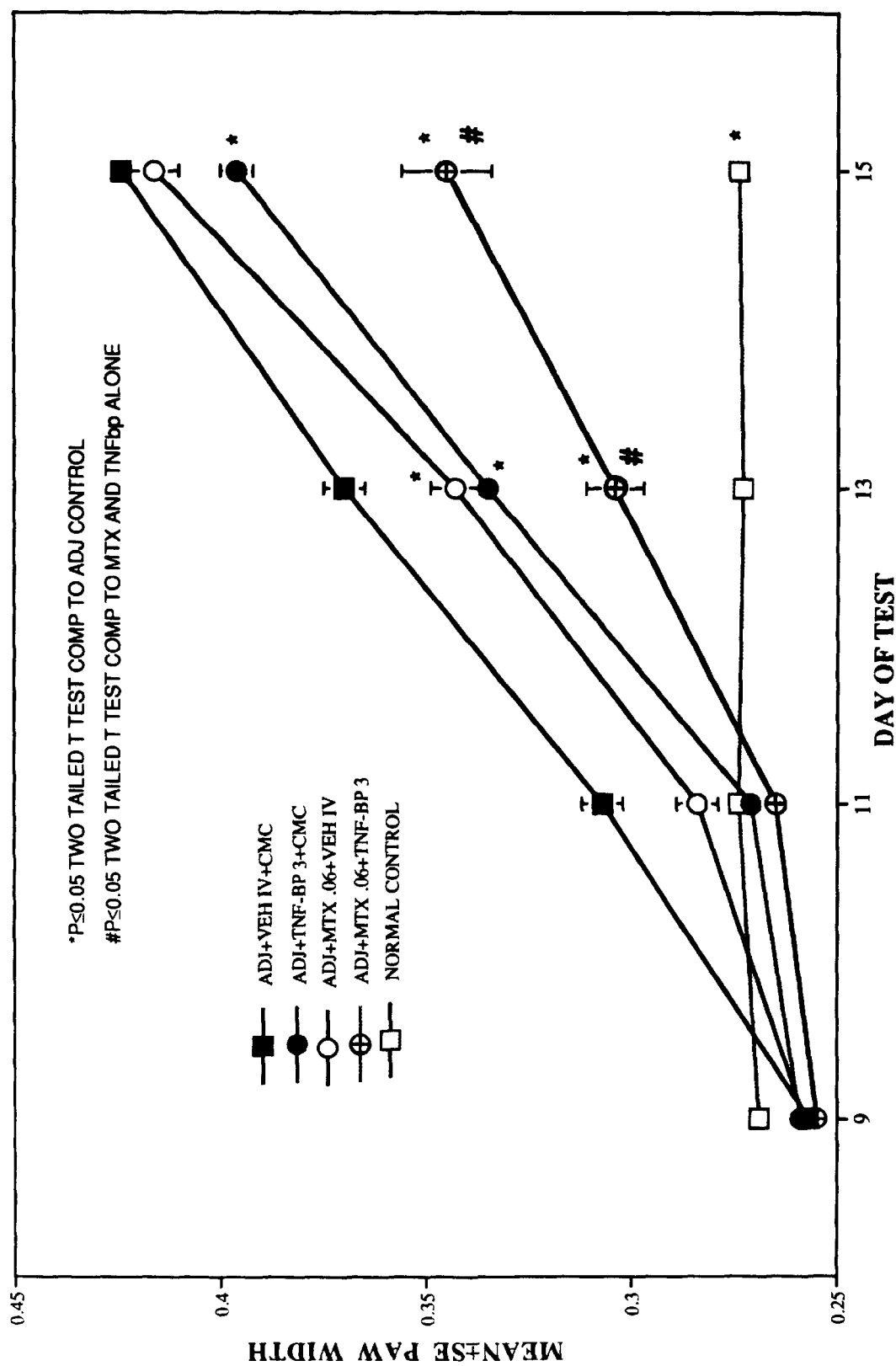
FIG. 3 depicts the effects of c105 sTNFR-I dumbbell alone, methotrexate alone and the combination of c105 sTNFR-I dumbbell and methotrexate on joint diameter in the adjuvant arthritic rats in Example 1.

The compositions and methods of the invention include administering to a patient afflicted with an inflammatory joint disease an effective amount of a TNF binding protein in combination with any of one or more anti-inflammatory drugs or therapies. The preferred patient is human.

TNF binding proteins are disclosed in the art (EP 308 378, EP 422 339, GB 2 218 101, EP 393 438, WO 90/13575, EP 398 327, EP 412 486, WO 91/03553, EP 418 014, JP 127,800/1991, EP 433 900, U.S. Pat. No. 5,136,021, GB 2 246 569, EP 464 533, WO 92/01002, WO 92/13095, WO 92/16221, EP 512 528, EP 526 905, WO 93/07863, EP 568 928, WO 93/21946, WO 93/19777, EP 417 563, WO 95/34326, WO 96/28546, and PCT Application No. PCT/US97/12244 the disclosures of which are hereby incorporated by reference).

For example, EP 393 438 and EP 422 339 teach the amino acid and nucleic acid sequences of a soluble TNF receptor type I (also known as sTNFR-I or 30 kDa TNF inhibitor) and a soluble TNF receptor type II (also known as sTNFR-II or 40 kDa TNF inhibitor), collectively termed "sTNFRs", as well as modified forms thereof (e.g., fragments, functional derivatives and variants). EP 393 438 and EP 422 339 also disclose methods for isolating the genes responsible for coding the inhibitors, cloning the gene in suitable vectors and cell types, and expressing the gene to produce the inhibitors.

sTNFR-I and sTNFR-II are members of the nerve growth factor/TNF receptor superfamily of receptors which includes the nerve growth factor receptor (NGF), the B cell antigen CD40, 4-1BB, the rat T-cell antigen MRC OX40, the fas antigen, and the CD27 and CD30 antigens (Smith et al. (1990), *Science*, 248:1019–1023). The most conserved feature amongst this group of cell surface receptors is the cysteine-rich extracellular ligand binding domain, which can be divided into four repeating motifs of about forty amino acids and which contains 4–6 cysteine residues at positions which are well conserved (Smith et al. (1990), supra).

For purposes of this invention, sTNFRs and modified forms thereof, including polypeptides in which amino acids of sTNFR-I and sTNFR-II have been deleted from ("deletion variants"), inserted into ("addition variants"), or substituted for ("substitution variants") are collectively termed "TNFbp(s)". [Unless otherwise indicated, amino acid numbering for molecules described herein shall correspond to that presented for the mature form of molecule (i.e., minus the signal sequence), as depicted by amino acids $Asp^1$-$Thr^{161}$ of SEQ ID NO:2, with any initial MET in each such sequence being residue number "0".]

It will be appreciated by those skilled in the art that many combinations of deletions, insertions and substitutions (individually or collectively "variant(s)") can be made within the amino acid sequences of the sTNFRs, provided that the resulting molecule is biologically active (e.g., possesses the ability to bind TNF).

An STNFR variant(s) may be rapidly screened to assess its physical properties. It will be appreciated that such variant(s) will demonstrate similar TNF inhibiting properties, but not necessarily all of the same properties and not necessarily to the same degree as the corresponding unmodified STNFR.

There are two principal variables in the construction of amino acid sequence variant(s): the location of the mutation site and the nature of the mutation. In designing variant(s), the location of each mutation site and the nature of each mutation will depend on the biochemical characteristic(s) to be modified. Each mutation site can be modified individually or in series, e.g., by (1) deleting the target amino acid residue, (2) inserting one or more amino acid residues adjacent to the located site or (3) substituting first with conservative amino acid choices and, depending upon the results achieved, then with more radical selections.

Amino acid sequence deletions generally range from about 1 to 30 amino acid residues, preferably from about 1 to 20 amino acid residues, more preferably from about 1 to 10 amino acid residues and most preferably from about 1 to 5 contiguous residues. Amino-terminal, carboxy-terminal and internal intrasequence deletions are contemplated. Deletions within the amino acid sequences of the sTNFRs may be made, for example, in regions of low homology with the sequences of other members of the NGF/TNF receptor family. Deletions within the amino acid sequences of the sTNFRs in areas of substantial homology with the sequences of other members of the NGF/TNF receptor family will be more likely to significantly modify the biological activity. Specifically, the sequence similarity among NGF/TNF receptor family members is particularly high in the region corresponding to the first two disulfide loops of domain 1, the whole of domain 2, and the first disulfide loop of domain 3 (Banner et al. (1993), *Cell*, 73:431–445). The number of total deletions and/or consecutive deletions preferably will be selected so as to preserve the tertiary structure in the affected domain, e.g., cysteine crosslinking.

EP 393 438 teaches a 40 kDa TNF inhibitor Δ51 and a 40 kDa TNF inhibitor Δ53, which are truncated versions of the full-length recombinant 40 kDa TNF inhibitor protein wherein 51 or 53 amino acid residues, respectively, at the carboxyl terminus of the mature protein are removed. Accordingly, a skilled artisan would appreciate that the fourth domain of each of the 30 kDa TNF inhibitor and the 40 kDa inhibitor is not necessary for TNF inhibition. In fact various groups have confirmed this understanding. Domain-deletion derivatives of the 30 kDa and 40 kDa TNF inhibitors have been generated, and those derivatives without the fourth domain retain full TNF binding activity while those derivatives without the first, second or third domain, respectively, do not retain TNF binding activity (Corcoran et al. (1994), *Eur. J. Biochem.*, 223:831–840; Chih-Hsueh et al. (1995), *The Journal of Biological Chemistry*, 270(6): 2874–2878; and Scallon et al. (1995), *Cytokine*, 7(8): 759–770).

PCT Application No. PCT/U.S.97/12244 teaches truncated forms of sTNFR-I and sTNFR-II which do not contain the fourth domain (amino acid residues $Thr^{127}$-$Asn^{161}$ of sTNFR-I and amino acid residues $Pro^{141}$-$Thr^{179}$ of sTNFR-II); a portion of the third domain (amino acid residues $Asn^{111}$-$Cys^{126}$ of sTNFR-I and amino acid residues $Pro^{123}$-$Lys^{140}$ of sTNFR-II); and, optionally, which do not contain a portion of the first domain (amino acid residues $Asp^{1}$-$Cys^{19}$ of sTNFR-I and amino acid residues $Leu^{1}$-$Cys^{32}$ of sTNFR-II). The truncated sTNFRs of the present invention include the proteins represented by the formula $R_1$-[$Cys^{19}$-$Cys^{103}$]-$R_2$ and $R_4$-[$Cys^{32}$-$Cys^{115}$]-$R_5$. These proteins are truncated forms of sTNFR-I and sTNFR-II, respectively.

By "$R_1$-[$Cys^{19}$-$Cys^{103}$]-$R_2$" is meant one or more proteins wherein [$Cys^{19}$-$Cys^{103}$] represents residues 19 through 103 of sTNFR-I, the amino acid residue numbering scheme of which is provided in FIG. 1 to facilitate the comparison; wherein $R_1$ represents a methionylated or nonmethionylated amine group of $Cys^{19}$ or of amino-terminus amino acid residue(s) selected from any one of $Cys^{18}$ to $Asp^1$ and wherein $R_2$ represents a carboxy group of $Cys^{103}$ or of carboxy-terminal amino acid residues selected from any one of $Phe^{104}$ to $Leu^{110}$.

Exemplary truncated sTNFR-I of the present invention include the following molecules (collectively termed 2.6 D sTNFR-I): $NH_2$-[$Asp^1$-$Cys^{105}$]-COOH (also referred to as sTNFR-I 2.6 D/C105); $NH_2$-[$Asp^1$-$Leu^{108}$]-COOH (also referred to as sTNFR-I 2.6 D/C106); $NH_2$-[$Asp^1$-$Asn^{105}$]-COOH (also referred to as sTNFR-I 2.6 D/N105); $NH_2$-[$Tyr^9$-$Leu^{108}$]-COOH (also referred to as sTNFR-I 2.3 D/d8); $NH_2$-[$Cys^{19}$-$Leu^{108}$]-COOH (also referred to as sTNFR-I 2.3 D/d18); and $NH_2$-[$Ser^{16}$-$Leu^{108}$]-COOH (also referred to as sTNFR-I 2.3 D/d15), either methionylated or nonmethionylated, and variants and derivatives thereof.

By "$R_3$-[$Cys^{32}$-$Cys^{115}$]-$R_4$" is meant one or more proteins wherein [$Cys^{32}$-$Cys^{115}$] represents residues $Cys^{32}$ through $Cys^{115}$ of sTNFR-II, the amino acid residue numbering scheme of which is provided in FIG. 2 to facilitate the comparison; wherein $R_3$ represents a methionylated or non-methionylated amine group of $Cys^{32}$ or of amino-terminus amino acid residue(s) selected from any one of $Cys^{31}$ to $Leu^1$ and wherein $R_4$ represents a carboxy group of $Cys^{115}$ or of carboxy-terminal amino acid residue(s) selected from any one of $Ala^{116}$ to $Arg^{122}$.

An amino acid sequence addition may include insertions of an amino- and/or carboxyl-terminal fusion ranging in length from one residue to one hundred or more residues, as well as internal intrasequence insertions of single or multiple amino acid residues. Internal additions may range generally from about 1 to 20 amino acid residues, preferably from about 1 to 10 amino acid residues, more preferably from about 1 to 5 amino acid residues, and most preferably from about 1 to 3 amino acid residues. Additions within the amino acid sequences of the sTNFRs may be made in regions of low homology with the sequences of other members of the NGF/TNF receptor family. Additions within the amino acid sequence of the sTNFRs in areas of substantial homology with the sequences of other members of the NGF/TNF receptor family will be more likely to significantly modify the biological activity. Additions preferably include amino acid sequences derived from the sequences of the NGF/TNF receptor family members.

An amino-terminus addition is contemplated to include the addition of a methionine (for example, as an artifact of the direct expression in bacterial recombinant cell culture). A further example of an amino-terminal addition includes the fusion of a signal sequence to the amino-terminus of mature sTNFRs in order to facilitate the secretion of protein from recombinant host cells. Such signal sequences generally will be obtained from and thus be homologous to the intended host cell species. For prokaryotic host cells that do not recognize and process the native signal sequence of the sTNFRs, the signal sequence may be substituted by a prokaryotic signal sequence selected, for example, from the group of the alkaline phosphatase, penicillinase or heat-stable enterotoxin II leader sequences. For expression in yeast cells the signal sequence may be selected, for example, from the group of the yeast invertase, alpha factor or acid phosphatase leader sequences. In mammalian cell expression the native signal sequences (EP 393 438 and EP 422 339) are satisfactory, although other mammalian signal sequences may be suitable, for example sequences derived from other NGF/TNP receptor family members.

An example of an amino- or a carboxy-terminus addition includes chimeric proteins comprising the amino-terminal or carboxy-terminal fusion of a TNFbp(s) with all or part of the constant domain of the heavy or light chain of human immunoglobulin (individually or collectively, ("sTNFR Fc(s)"). Such chimeric polypeptides are preferred wherein the immunoglobulin portion of each comprises all of the domains except the first domain of the constant region of the heavy chain of human immunoglobulin such as IgG (e.g., IgG1 or IgG3), IgA, IgM or IgE. A skilled artisan will appreciate that any amino acid of the immunoglobulin portion can be deleted or substituted with one or more amino acids, or one or more amino acids can be added as long as the TNF binding protein portion still binds TNF and the immunoglobulin portion shows one or more of its characteristic properties.

Another group of variant(s) is amino acid substitution variant(s) of the amino acid sequence of sTNFRs. These are variant(s) wherein at least one amino acid residue in an sTNFR is removed and a different residue inserted in its place. Substitution variant(s) include allelic variant(s) which are characterized by naturally-occurring nucleotide sequence changes in the species population that may or may not result in an amino acid change. One skilled in the art can use any information known about the binding or active site of the polypeptide in the selection of possible mutation sites.

One method for identifying amino acid residues or regions for mutagenesis of a protein is called "alanine scanning mutagenesis", as described by Cunningham and Wells (1989), $Science$, 244:1081–1085, the disclosure of which is hereby incorporated by reference. In this method, an amino acid residue or group of target residues is identified (e.g., charged residues such as Arg, Asp, His, Lys and Glu) and replaced by a neutral or negatively-charged amino acid (most preferably alanine or polyalanine) to affect the interaction of the amino acids with the surrounding aqueous environment in or outside the cell. Those domains/residues demonstrating functional sensitivity to the substitutions are then refined by introducing additional or alternate residues at the sites of substitution. Thus, the site for introducing an amino acid sequence modification is predetermined. To optimize the performance of a mutation at a given site, alanine scanning or random mutagenesis may be conducted and the variant(s) may be screened for the optimal combination of desired activity and degree of activity.

The sites of greatest interest for substitutional mutagenesis include sites in which particular amino acid residues within an sTNFR are substantially different from other species or or other NGF/TNF receptor family members in terms of side-chain bulk, charge and/or hydrophobicity. Other sites of interest include those in which particular residues of an sTNFR are identical among other species or other NGF/TNF receptor family members, as such positions are generally important for the biological activity of a protein.

Other sites of interest include those in which particular residues are similar or identical with those of such sTNFR-I-like proteins and sTNFR-II-like proteins. Accordingly, the following information has been elucidated concerning sTNFR-I (Banner et al. (1993), supra, and Fu et al. (1995), $Protein Engineering$, 8(12):1233–1241). Residues $Tyr^9$, $Thr^{39}$, $His^{55}$ in Domain 1, residues $Phe^{49}$, $Ser^{63}$, $Asp^{82}$ in Domain 2 and residues $Tyr^{92}$ and $Ser^{107}$ in Domain 3 have been identified as being potentially important for the stabilization of the structure of Domains 1, 2 and 3, respectively. Residues $Pro^{12}$ and $His^{55}$ have been identified as potentially interacting with $Ser^{86}$-$Tyr^{87}$ on subunit C of TNF-α. Residues $Glu^{45}$-$Phe^{49}$ have been identified as being in a loop which potentially interacts with residues $Leu^{29}$-$Arg^{32}$ of TNF-α subunit A. Residues $Gly^{48}$ has been identified as potentially interacting with $Asn^{19}$-$Pro^{20}$ on subunit A of TNF-α. Residue $His^{58}$-$Leu^{60}$ have been identified as being in an extended strand conformation and side chain interactions with residues $Arg^{31}$-$Ala^{33}$ on subunit A of TNF-α have been potentially identified with residue $His^{58}$ of sTNFR-I specifically interacting with residue $Arg^{31}$. Residues $Lys^{64}$-$Arg^{66}$ have been identified as being in an extended strand conformation and have been identified as having side chain and main chain interactions with residues $Ala^{145}$-$Glu^{146}$ and residue $Glu^{46}$ on subunit A of TNF-α. Residue $Met^{69}$ has been identified as potentially interacting with residue $Tyr^{115}$ on subunit A of TNF-α. Residues $His^{94}$-$Phe^{101}$ have been identified as forming a loop which interacts with residues $Thr^{72}$-$Leu^{75}$ and $Asn^{137}$ of subunit C of TNF-α, with residue $Trp^{96}$ of sTNFR-I specifically interacting with residues $Ser^{71}$-$Thr^{72}$ on subunit C of TNF-α, $Leu^{100}$ of STNFR-I being in close proximity with residue $Asn^{137}$ on subunit C of TNF-α and residue $Gln^{102}$ of sTNFR-I specifically interacting with residue $Pro^{113}$ on subunit A of TNF-α.

In addition to the cysteines forming the 3 pairs of disulfide bonds within each of the four domains of the molecule, there are several other conserved residues that contribute to the stabilization of the tertiary fold of each domain.

There are two main classes into which these stabilizing residues fall. The first type contributes to the shielding of the disulfide bond sulfur atoms from solvent. An example of this residues in domain 3 is $Tyr^{92}$. In domain 4 $Phe^{133}$ helps to shield the $Cys^{128}$-$Cys^{139}$ disulfide bond. All four domains have either a Tyr or Phe at these same structurally conserved locations. The second class of stabilizing residues form hydrogen bonds within their respective domains. Within domain 3 $Asn^{123}$ and $Ser^{107}$ form a hydrogen bond and $Ser^{107}$ forms an additional hydrogen bond with $Thr^{124}$. For domain 4 these residues include $Asn^{144}$ and $Ser^{141}$.

In addition there are hydrogen bonds between domain 3 and 4 that are not seen between other domains. These hydrogens bonds are (1) $Asn^{105}$ main-chain oxygen and $Asn^{137}$ side-chain nitrogen and (2) $Ser^{107}$ side-chain oxygen and $Asn^{137}$ main-chain nitrogen.

A skilled artisan will appreciate that initially the sites should be modified by substitution in a relatively conservative manner. Such conservative substitutions are shown in Table 1 under the heading of "Preferred Substitutions". If such substitutions result in a change in biological activity, then more substantial changes (Exemplary Substitutions) may be introduced and/or other additions/deletions may be made and the resulting products screened.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |

TABLE 1-continued

Amino Acid Substitutions

| Original Residue | Preferred Substitutions | Exemplary Substitutions |
|---|---|---|
| Tyr (Y) | Phe | Trp; Phe; Thr; Ser |
| Val (V) | Leu | Ile; Leu; Met; Phe; Ala; norleucine |

In making such changes, the hydropathic index of amino acids may be considered. The importance of the hydropathic amino acid index in conferring interactive biological function on a protein is generally understood in the art (Kyte and Doolittle (1982), *J. Mol. Biol.*, 157:105–131, the disclosure of which is incorporated herein by reference). It is known that certain amino acids may be substituted for other amino acids having a similar hydropathic index or score and still retain a similar biological activity.

It is also understood in the art that the substitution of like amino acids can be made effectively on the basis of hydrophilicity, particularly where the functionally equivalent protein or peptide thereby created is intended for use in immunological embodiments, as in the present case. U.S. Pat. 4,554,101, the disclosure of which is incorporated herein by reference, states that the greatest local average hydrophilicity of a protein, as governed by the hydrophilicity of its adjacent amino acids, correlates with its immunogenicity and antigenicity, i.e., with a biological property of the protein.

U.S. Pat. 4,554,101 also teaches the identification and preparation of epitopes from primary amino acid sequences on the basis of hydrophilicity. Through the methods disclosed in U.S. Pat. 4,554,101 a skilled artisan would be able to identify epitopes, for example, within the amino acid sequence of an sTNFR. These regions are also referred to as "epitopic core regions". Numerous scientific publications have been devoted to the prediction of secondary structure, and to the identification of epitopes, from analyses of amino acid sequences (Chou and Fasman (1974), *Biochemistry*, 13(2):222–245; Chou and Fasman (1974), *Biochemistry*, 13(2):211–222; Chou and Fasman (1978), *Adv. Enzymol. Relat. Areas Mol. Biol.*, 47:45–148; Chou and Fasman (1978), *Ann. Rev. Biochem.*, 47:251–276 and Chou and Fasman (1979), *Biophys. J.*, 26:367–384, the disclosures of which are incorporated herein by reference). Moreover, computer programs are currently available to assist with predicting antigenic portions and epitopic core regions of proteins. Examples include those programs based upon the Jameson-Wolf analysis (Jameson and Wolf (1988), *Comput. Appl. Biosci.*, 4(1):181–186 and Wolf et al. (1988), *Comput. Appl. Biosci.*, 4(1):187–191, the disclosures of which are incorporated herein by reference); the program PepPlot® (Brutlag et al. (1990), *CABS*, 6:237–245 and Weinberger et al. (1985), *Science*, 228:740–742, the disclosures of which are incorporated herein by reference); and other programs for protein tertiary structure prediction (Fetrow and Bryant (1993), *BIOTECHNOLOGY*, 11:479–483, the disclosure of which is incorporated herein by reference).

In contrast, substantial modifications in the functional and/or chemical characteristics of the sTNFRs may be accomplished by selecting substitutions that differ significantly in their effect on maintaining (a) the structure of the polypeptide backbone in the area of the substitution, for example, as a sheet or helical conformation, (b) the relative charge or hydrophobicity of the protein at the target site or (c) the bulk of the side chain. Naturally-occurring residues are divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) aromatic: Trp, Tyr, Phe; and
6) residues that influence chain orientation: Gly, Pro.

Non-conservative substitutions may involve the exchange of a member of one of these groups for another. Such substituted residues may be introduced into regions of the sTNFRs that, for example, are homologous with other NGF/TNF receptor family members or into non-homologous regions of the protein.

A variety of amino acid substitutions or deletions may be made to modify or add N-linked or O-linked glycosylation sites, resulting in a protein with altered glycosylation. The sequence may be modified to add glycosylation sites to or to delete N-linked or O-linked glycosylation sites from the sTNFRs. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. Proven or predicted asparagine residues of 30 kDa TNF inhibitor exist at positions 14, 105 and 111.

Specific mutations of the sequences of the sTNFRs may involve substitution of a non-native amino acid at the amino-terminus, carboxy-terminus or at any site of the protein that is modified by the addition of an N-linked or O-linked carbohydrate. Such modifications may be of particular utility in the addition of an amino acid (e.g., cysteine), which is advantageous for the linking of a water soluble polymer to form a derivative. For example, WO 92/16221 describes the preparation of sTNFR-I muteins, e.g., wherein an asparagine residue at position 105 of the native human protein is changed to cysteine (c105 sTNFR-I).

In a specific embodiment, a variant polypeptide will preferably be substantially homologous to the amino acid of the sTNFR from which it is derived. The term "substantially homologous" as used herein means a degree of homology that is in excess of 80%, preferably in excess of 90%, more preferably in excess of 95% or most preferably even 99%. The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff (1972), *Atlas of Protein Sequence and Structure*, 5:124, National Biochemical Research Foundation, Washington, D.C., the disclosure of which is hereby incorporated by reference. Also included within the term "substantially homologous" are variant(s) of sTNFRs which may be isolated by virtue of cross-reactivity with antibodies to the amino acid sequences of SEQ ID NO:2 and SEQ ID NO:4 or whose genes may be isolated through hybridization with the DNA of SEQ ID NO:1 and SEQ ID NO:3 or with segments thereof.

Polypeptide Derivatives

Chemically-modified derivatives of the TNFbp(s) in which the protein is linked to a polymer in order to modify properties of the protein (referred herein as "derivatives")

are included within the scope of the present invention. Such derivatives may be prepared by one skilled in the art given the disclosures herein. Conjugates may be prepared using glycosylated, non-glycosylated or de-glycosylated TNFbp(s) and suitable chemical moieties. Typically non-glycosylated proteins and water soluble polymers will be used.

Water soluble polymers are desirable because the protein to which each is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the therapeutic profile of the protein (e.g., duration of sustained release; resistance to proteolysis; effects, if any, on dosage; biological activity; ease of handling; degree or lack of antigenicity and other known effects of a water soluble polymer on a therapeutic proteins).

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone)polyethylene glycol, polypropylene glycol homopolymers (PPG) and other polyalkylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof. As used herein, polyethylene glycol is meant to encompass any of the forms that have been used to derivatize other proteins, such as mono-(C1–C10) alkoxy- or aryloxy-polyethylene glycol. Polyethylene glycol propionaldehyde may have advantages in manufacturing due to its stability in water.

The water soluble polymers each may be of any molecular weight and may be branched or unbranched. Generally, the higher the molecular weight or the more branches, the higher the polymer:protein ratio. The water soluble polymers each typically have an average molecular weight of between about 2 kDa to about 100 kDa (the term "about" indicating that in preparations of a water soluble polymer, some molecules will weigh more, some less, than the stated molecular weight). The average molecular weight of each water soluble polymer preferably is between about 5 kDa and about 40 kDa, more preferably between about 10 kDa and about 35 kDa and most preferably between about 15 kDa and about 30 kDa.

There are a number of attachment methods available to those skilled in the art, including acylation reactions or alkylation reactions (preferably to generate an amino-terminal chemically modified protein) with a reactive water soluble molecule. See, for example, EP 0 401 384; Malik et al. (1992), *Exp. Hematol.*, 20:1028–1035; Francis (1992), *Focus on Growth Factors*, 3(2):4–10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459 and the other publications cited herein that relate to pegylation, the disclosures of which are hereby incorporated by reference.

A specific embodiment of the present invention is an unbranched monomethoxy-polyethylene glycol aldehyde molecule having an average molecular weight of either about 20 kDa or about 33 kDa (e.g., between 30 kDa and 35 kDa), or a tertiary-butyl polyethylene glycol aldehyde having an average molecular weight of about 33 kDa (e.g., between 30 kDa and 35 kDa) conjugated via reductive alkylation to the TNFbp(s).

The pegylation also may be specifically carried out using water soluble polymers having at least one reactive hydroxy group (e.g. polyethylene glycol). The water soluble polymer can be reacted with an activating group, thereby forming an "activated linker" useful in modifying various proteins. The activated linkers can be monofunctional, bifunctional, or multifunctional.

Activating groups which can be used to link the water soluble polymer to two or more proteins include the following: sulfone, maleimide, sulfhydryl, thiol, triflate, tresylate, azidirine, oxirane and 5-pyridyl. Useful reagents having a reactive sulfone group that can be used in the methods include, without limitation, chlorosulfone, vinylsulfone and divinylsulfone. These PEG derivatives are stable against hydrolysis for extended periods in aqueous environments at pHs of about 11 or less, and can form linkages with molecules to form conjugates which are also hydrolytically stable. Two particularly useful homobifunctional derivatives are PEG-bis-chlorosulfone and PEG-bis-vinylsulfone (WO 95/13312).

WO 97/04003, the disclosure of which is hereby incorporated by reference, teaches methods of making sulfone-activated linkers by obtaining a compound having a reactive hydroxyl group and converting the hydroxyl group to a reactive Michael acceptor to form an activated linker, with the use of tetrahydrofuran (THF) as the solvent for the conversion. The application also teaches a process for purifying the activated linkers which utilizes hydrophobic interaction chromatography to separate the linkers based on size and end-group functionality.

Polyvalent Forms

Polyvalent forms, i.e., molecules comprising more than one active moiety, may be constructed. In one embodiment, the molecule may possess multiple tumor necrosis factor binding sites for the TNF ligand. Additionally, the molecule may possess at least one tumor necrosis factor binding site and, depending upon the desired characteristic of polyvalent form, at least one site of another molecule (e.g., a TNFbp(s), and an interleukin-1 receptor antagonist ("IL-1ra") as described below).

In one embodiment, the polyvalent form may be constructed, for example, by chemically coupling at least one TNFbp(s) and another moiety with any clinically accepted linker (e.g., a water-soluble polymer). In principle the linker must not impart new immunogenecity nor, by virtue of the new amino acid residues, alter the hydrophobicity and charge balance of the structure which affects its biodistribution and clearance.

The water soluble polymers can be, based on the monomers listed herein, homopolymers, random or block copolymers, terpolymers straight chain or branched, substituted or unsubstituted. The polymer can be of any length or molecular weight, but these characteristics can affect the biological properties. Polymer average molecular weights particularly useful for decreasing clearance rates in pharmaceutical applications are in the range of 2,000 to 35,000 daltons. In addition, the length of the polymer can be varied to optimize or confer the desired biological activity.

The active moieties may be linked using conventional coupling techniques (see WO 92/16221, WO 95/13312 and WO 95/34326, the disclosures of which are hereby incorporated by reference). For example, WO 92/16221 and WO 95/34326 describe the preparation of various dimerized sTNFR-I molecules, e.g., dimerized c105 STNFR-I.

Alternatively, a bivalent molecule may consist of two tandem repeats of sTNFRs separated by a polypeptide linker region. The design of the polypeptide linkers is similar in design to the insertion of short loop sequences between domains in the de novo design of proteins (Mutter (1988), *TIBS*, 13:260–265 and Regan and DeGrado (1988), *Science*, 241:976–978, the disclosures of which are hereby incorporated by reference). Several different linker constructs have been assembled and shown to be useful for forming single chain antibodies; the most functional linkers vary in size from 12 to 25 amino acids (amino acids having unreactive side groups, e.g., alanine, serine and glycine) which together constitute a hydrophilic sequence, have a few oppositely charged residues to enhance solubility and are flexible (Whitlow and Filpula (1991), *Methods: A Companion to Methods in Enzymology*, 2:97–105; and Brigido et al. (1993), *J. Immunol.*, 150:469–479, the disclosures of which are hereby incorporated by reference). It has been shown that a linker suitable for single chain antibodies is effective to produce a dimeric form of the human sTNFR-II (Neve et al. (1996), *Cytokine*, 8(5):365–370, the disclosure of which is hereby incorporated by reference).

Additionally, a TNFbp(s) may be chemically coupled to biotin, and the resulting conjugate may then be allowed to bind to avidin, resulting in tetravalent avidin/biotin/TNFbp (s) molecules. A TNFbp(s) may also be covalently coupled to dinitrophenol (DNP) or trinitrophenol (TNP) and the resulting conjugates precipitated with anti-DNP or anti-TNP-IgM to form decameric conjugates.

In yet another embodiment, recombinant fusion proteins may also be produced wherein each recombinant chimeric molecule has a TNFbp(s) sequence amino-terminally or carboxy-terminally fused to all or part of the constant domains, but at least one constant domain, of the heavy or light chain of human immunoglobulin. For example, a chimeric TNFbp(s)/IgG1 (or IgG1/TNFbp(s)) fusion protein may be produced from a light chain-containing chimeric gene: a TNFbp(s)/human kappa light chain chimera (TNFbp (s)/Ck) or a human kappa light chain/TNFbp(s) chimera (Ck/TNFbp(s)); or a heavy chain-containing chimeric gene: a TNFbp(s)/human gamma-1 heavy chain chimera (TNFbp (s)/Cg-1) or a human gamma-1 heavy chain/TNFbp(s) chimera (Cg-1/TNFbp(s)). Following transcription and translation of a heavy-chain chimeric gene, or of a light chain-containing gene and a heavy-chain chimeric gene, the gene products may be assembled into a single chimeric molecule having a TNFbp(s) displayed bivalently. Additional details relating to the construction of such chimeric molecules are disclosed in U.S. Pat. 5,116,964, WO 89/09622, WO 91/16437 and EP 315062, the disclosures of which are hereby incorporated by reference.

In yet a further embodiment, recombinant fusion proteins may also be produced wherein each recombinant chimeric molecule has at least one TNFbp(s), as described herein, and at least a portion of the region 186–401 of osteoprotogerin, as described in European Patent Application No. 96309363.8, the disclosures of which are hereby incorporated by reference. Either the TNFbp(s) or the portion of osteoprotogerin may be at the amino-terminus or the carboxy-terminus of the chimeric molecule.

Synthesis of TNFbp(s)

The production of TNFbp(s) is described in further detail below. Such proteins may be prepared, for example, by recombinant techniques or by in vitro chemical synthesis.

Polynucleotides

Based upon the present description and using the universal codon table, one of ordinary skill in the art can readily determine all of the nucleic acid sequences which encode the amino acid sequence of the TNFbp(s).

Recombinant expression techniques conducted in accordance with the descriptions set forth below may be followed to produce each such polynucleotide and to express the encoded proteins. For example, by inserting a nucleic acid sequence which encodes a TNFbp(s) into an appropriate vector, one skilled in the art can readily produce large quantities of the desired nucleotide sequence. The sequences can then be used to generate detection probes or amplification primers. Alternatively, a polynucleotide encoding a TNFbp(s) can be inserted into an expression vector. By introducing the expression vector into an appropriate host, the desired protein may be produced in large amounts.

As further described herein, there are numerous host/vector systems available for the propagation of desired nucleic acid sequences and/or the production of the desired proteins. These include, but are not limited to, plasmid, viral and insertional vectors, and prokaryotic and eukaryotic hosts. One skilled in the art can adapt a host/vector system which is capable of propagating or expressing heterologous DNA to produce or express the sequences of the present invention.

Furthermore, it will be appreciated by those skilled in the art that, in view of the present disclosure, the nucleic acid sequences within the scope of the present invention include the nucleic acids of FIGS. 1 and 3, as well as degenerate nucleic acid sequences thereof, nucleic acid sequences which encode variant(s) of the sTNFRs, and those nucleic acid sequences which hybridize to complements of the nucleic acids of FIGS. 1 and 3 under hybridization conditions, or equivalent conditions thereto, disclosed in the cDNA library screening section below.

Also provided by the present invention are recombinant DNA constructs involving vector DNA together with the DNA sequences encoding the desired proteins. In each such DNA construct, the nucleic acid sequence encoding a desired protein (with or without signal peptides) is in operative association with a suitable expression control or regulatory sequence capable of directing the replication and/or expression of the desired protein in a selected host.

Recombinant Expression

Preparation of Polynucleotides

A nucleic acid sequence encoding a TNFbp(s) can readily be obtained in a variety of ways including, without limitation, chemical synthesis, cDNA or genomic library screening, expression library screening and/or PCR amplification of cDNA. These methods and others which are useful for isolating such nucleic acid sequences are set forth in Sambrook et al. (1989), *Molecular Cloning: A Laboratory Manual,* Cold Spring Harbor Laboratory Press, Cold Spring Harbor, N.Y.; by Ausubel et al. (1994), Current Protocols in *Molecular Biology,* Current Protocols Press; and by Berger and Kimmel (1987), *Methods in Enzymology: Guide to Molecular Cloning Techniques,* Vol. 152, Academic Press, Inc., San Diego, Calif., the disclosures of which are hereby incorporated by reference.

Chemical synthesis of a nucleic acid sequence which encodes a desired protein can be accomplished using methods well known in the art, such as those set forth by Engels et al. (1989), *Angew. Chem. Intl. Ed.,* 28:716–734 and Wells et al. (1985), *Gene,* 34:315, the disclosures of which is hereby incorporated by reference. These methods include, inter alia, the phosphotriester, phosphoramidite and H-phosphonate methods of nucleic acid sequence synthesis. Large nucleic acid sequences, for example those larger than about 100 nucleotides in length, can be synthesized as several fragments. The fragments can then be ligated together to form a suitable nucleic acid sequence. A preferred method is polymer-supported synthesis using standard phosphoramidite chemistry.

Alternatively, a suitable nucleic acid sequence may be obtained by screening an appropriate cDNA library (i.e., a library prepared from one or more tissue sources believed to express the protein) or a genomic library (a library prepared from total genomic DNA). The source of the cDNA library is typically a tissue or cell source from any species that is believed to express a desired protein in reasonable quantities. The source of the genomic library may be any tissue or tissues from any mammalian or other species believed to harbor a gene encoding a desired protein.

Each hybridization medium can be screened for the presence of a DNA encoding a desired protein using one or more nucleic acid probes (oligonucleotides, cDNA or genomic DNA fragments that possess an acceptable level of homology to the cDNA or gene to be cloned) that will hybridize selectively with cDNA(s) or gene(s) present in the library. The probes typically used for such screening encode a small region of DNA sequence from the same or a similar species as the species from which the library is prepared. Alternatively, the probes may be degenerate, as discussed herein.

Hybridization is typically accomplished by annealing the oligonucleotide probe or cDNA to the clones under conditions of stringency that prevent non-specific binding but permit binding of those clones that have a significant level of homology with the probe or primer. Typical hybridization and washing stringency conditions depend in part on the size (i.e., number of nucleotides in length) of the cDNA or oligonucleotide probe and whether the probe is degenerate. The probability of identifying a clone is also considered in designing the hybridization medium (e.g., whether a cDNA or genomic library is being screened).

Where a DNA fragment (such as cDNA) is used as a probe, typical hybridization conditions include those as set forth in Ausubel et al. (1994), supra. After hybridization, the hybridization medium is washed at a suitable stringency, depending on several factors such as probe size, expected homology of probe to clone, the hybridization medium being screened, the number of clones being screened and the like.

Exemplary stringent hybridization conditions are hybridization in 6×SSC at 62–67° C., followed by washing in 0.1×SSC at 62–67° C. for approximately one hour. Alternatively, exemplary stringent hybridization conditions are hybridization at 45–55% formamide, 6×SSC at 40–45° C., followed by washing in 0.1×SSC at 62–67° C. for approximately one hour. Also included are DNA sequences which hybridize to the nucleic acid sequences set forth in FIGS. 1 and 3 under relaxed hybridization conditions and which encode a TNFbp(s). Examples of such relaxed stringency hybridization conditions are 6×SSC at 45–55° C. or hybridization with 30–40% formamide at 40–45° C., followed by washing in 1–2×SSC at 55° C. for approximately 30 minutes. See Maniatis et al. (1982), *Molecular Cloning (A Laboratory Manual)*, Cold Spring Harbor Laboratory, pages 387 to 389, the disclosure of which is hereby incorporated by reference.

There are also exemplary protocols for stringent washing conditions where oligonucleotide probes are used to screen hybridization media. For example, a first protocol uses 6×SSC with 0.05 percent sodium pyrophosphate at a temperature of between about 35° C. and 63° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0 and 0.2% SDS.

Another method for obtaining a suitable nucleic acid sequence encoding a TNFbp(s) is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding the desired protein, are then added to the cDNA along with a polymerase such as Taq polymerase and the polymerase amplifies the cDNA region between the two primers.

The oligonucleotide sequences selected as probes or primers should be of adequate length and sufficiently unambiguous so as to minimize the amount of non-specific binding that may occur during screening or PCR amplification. The actual sequence of the probes or primers is usually based on conserved or highly homologous sequences or regions. Optionally, the probes or primers can be fully or partially degenerate, i.e., can contain a mixture of probes/primers, all encoding the same amino acid sequence but using different codons to do so. An alternative to preparing degenerate probes is to place an inosine in some or all of those codon positions that vary by species. The oligonucleotide probes or primers may be prepared by chemical synthesis methods for DNA, as described herein.

Vectors

DNA encoding the desired proteins may be inserted into vectors for further cloning (amplification of the DNA) or for expression. Suitable vectors are commercially available or may be specifically constructed. The selection or construction of an appropriate vector will depend on (1) whether it is to be used for DNA amplification or for DNA expression, (2) the size of the DNA to be inserted into the vector and (3) the intended host cell to be transformed with the vector.

The vectors each typically involve a nucleic acid sequence which encodes a desired protein operatively linked to one or more of the following expression control or regulatory sequences capable of directing, controlling or otherwise effecting the expression of a desired protein by a selected host cell. Each vector contains various components, depending on its function (amplification of DNA or expression of DNA) and its compatibility with the intended host cell. The vector components generally include, but are not limited to, one or more of the following: a signal sequence, an origin of replication, one or more selection or marker genes, a promoter, an enhancer element, a transcription termination sequence and the like. These components may be obtained from natural sources or be synthesized by known procedures.

Examples of suitable prokaryotic cloning vectors include bacteriophages such as lambda derivatives, or plasmids from *E. coli* (e.g. pBR322, col E1, pUC, the F-factor and Bluescript® plasmid derivatives (Stratagene, La Jolla, Calif.)). Other appropriate expression vectors, of which numerous types are known in the art for the host cells described below, can also be used for this purpose.

Signal Sequence

The nucleic acid encoding a signal sequence may be inserted 5' of the sequence encoding a desired protein, e.g, it may be a component of a vector or it may be a part of a nucleic acid encoding a desired protein. The nucleic acids encoding the native signal sequences of the sTNFRs are known (EP 393 438, EP 422 339 and WO 96/28546, the disclosures of which are hereby incorporated by reference).

Origin of Replication

Expression and cloning vectors each generally include a nucleic acid sequence that enables the vector to replicate in one or more selected host cells. In a cloning vector, this sequence is typically one that enables the vector to replicate independently of the host chromosomal DNA and includes an origin of replication or autonomously replicating sequence. Such sequences are well known. The origin of replication from the plasmid pBR322 is suitable for most Gram-negative bacteria, and various origins (e.g., Simian Virus 40 (SV40), polyoma, adenovirus, VSV or BPV) are useful for cloning vectors in mammalian cells. Generally, the origin of replication is not needed for mammalian expression vectors (for example, the SV40 origin is often used only because it contains the early promoter).

Selection Gene

The expression and cloning vectors each typically contain a selection gene. This gene encodes a "marker" protein necessary for the survival or growth of the transformed host cells when grown in a selective culture media. Host cells that are not transformed with the vector will not contain the selection gene and, therefore, will not survive in the culture media. Typical selection genes encode proteins that (a) confer resistance to antibiotics or other toxins, e.g., ampicillin, neomycin, methotrexate or tetracycline; (b) complement auxotrophic deficiencies; or (c) supply critical nutrients not available from the culture media.

Other selection genes may be used to amplify the genes to be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The cell transformants are placed under selection pressure which only the transformants are uniquely adapted to survive by virtue of the marker being present in the vector. Selection pressure is imposed by culturing the transformed cells under conditions in which the concentration of selection agent in the media is successively changed, thereby leading to amplification of both the selection gene and the DNA that encodes the desired protein. As a result, increased quantities of the desired protein are synthesized from the amplified DNA.

For example, cells transformed with the DHFR selection gene are first identified by culturing all of the transformants in a culture media that contains methotrexate, a competitive antagonist of DHFR. An appropriate host cell when wild-type DHFR is used is the Chinese hamster ovary cell line deficient in DHFR activity (Urlaub and Chasin (1980), *Proc. Natl. Acad. Sci., USA,* 77(7):4216–4220, the disclosure of which is hereby incorporated by reference). The transformed cells are then exposed to increased levels of methotrexate. This leads to the synthesis of multiple copies of the DHFR gene and, concomitantly, multiple copies of other DNA present in the expression vector, such as the DNA encoding a desired protein.

Promoter

Expression and cloning vectors each will typically contain a promoter that is recognized by the host organism and is operably linked to a nucleic acid sequence encoding the desired protein. A promoter is an untranslated sequence located upstream (5') to the start codon of a structural gene (generally within about 100 to 1000 bp) that controls the transcription and translation of a particular nucleic acid sequence. A promoter may be conventionally grouped into one of two classes, inducible promoters and constitutive promoters. An inducible promoter initiates increased levels of transcription from DNA under its control in response to some change in culture conditions, such as the presence or absence of a nutrient or a change in temperature. A large number of promoters, recognized by a variety of potential host cells, are well known. A promoter may be operably linked to DNA encoding a desired protein by removing the promoter from the source DNA by restriction enzyme digestion and inserting the desired promoter sequence. The native promoter sequences of sTNFRs may be used to direct amplification and/or expression of the DNA encoding a desired protein. A heterologous promoter is preferred, however, if it permits greater transcription and higher yields of the expressed protein as compared to the native promoter and if it is compatible with the host cell system that has been selected for use. For example, any one of the native promoter sequences of other NGF/TNF receptor family members may be used to direct amplification and/or expression of the DNA encoding a desired protein.

Promoters suitable for use with prokaryotic hosts include the beta-lactamase and lactose promoter systems; alkaline phosphatase; a tryptophan (trp) promoter system; a bacterial luminescence (luxR) gene system and hybrid promoters such as the tac promoter. Other known bacterial promoters are also suitable. Their nucleotide sequences have been published, thereby enabling one skilled in the art to ligate each selected sequence to the desired DNA sequence using linkers or adaptors as needed to supply any required restriction sites.

Suitable promoter sequences for use with yeast hosts are also well known in the art. Suitable promoters for use with mammalian host cells are well known and include those obtained from the genomes of viruses such as polyoma virus, fowlpox virus; adenovirus (such as Adenovirus 2), bovine papilloma virus, avian sarcoma virus, cytomegalovirus, a retrovirus, hepatitis-B virus and, most preferably, SV40. Other suitable mammalian promoters include heterologous mammalian promoters, e.g., heat-shock promoters and the actin promoter.

Enhancer Element

The expression and cloning vectors each will typically contain an enhancer sequence to increase the transcription by higher eukaryotes of a DNA sequence encoding a desired protein. Enhancers are cis-acting elements of DNA, usually from about 10–300 bp in length, that act on the promoter to increase its transcription. Enhancers are relatively orientation and position independent. They have been found 5' and 3' to the transcription unit. Yeast enhancers are advantageously used with yeast promoters. Several enhancer sequences available from mammalian genes are known (e.g., globin, elastase, albumin, alpha-feto-protein and insulin). Additionally, viral enhancers such as the SV40 enhancer, the cytomegalovirus early promoter enhancer, the polyoma enhancer and adenovirus enhancers are exemplary enhancing elements for the activation of eukaryotic promoters. While an enhancer may be spliced into a vector at a position 5' or 3' to a DNA encoding a desired protein, it is typically located at a site 5' from the promoter.

Transcription Termination

Expression vectors used in eukaryotic host cells each will typically contain a sequence necessary for the termination of transcription and for stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding a desired protein.

Vector Construction

The construction of a suitable vector containing one or more of the herein-listed components (together with the desired coding sequence) may be accomplished by standard ligation techniques. Isolated plasmids or DNA fragments are cleaved, tailored and religated in the desired order to generate the required vector. To confirm that the correct sequence has been constructed, the ligation mixture may be used to transform E. coli, and successful transformants may be selected by known techniques as described herein. Quantities of the vector from the transformants are then prepared, analyzed by restriction endonuclease digestion and/or sequenced to confirm the presence of the desired construct.

A vector that provides for the transient expression of DNA encoding a desired protein in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Each transient expression system, comprising a suitable expression vector and a host cell, allows for the convenient positive identification of proteins encoded by cloned DNAs, as well as for the rapid screening of such proteins for desired biological or physiological properties.

Host Cells

Any of a variety of recombinant host cells, each of which contains a nucleic acid sequence for use in expressing a desired protein, is also provided by the present invention. Exemplary prokaryotic and eukaryotic host cells include bacterial, mammalian, fungal, insect, yeast or plant cells.

Prokaryotic host cells include, but are not limited to, eubacteria such as Gram-negative or Gram-positive organisms (e.g., E. coli (HB101, DH5a, DH10, and MC1061); Bacilli spp. such as B. subtilis; Pseudomonas spp. such as P. aeruginosa; Streptomyces spp.; Salmonella spp. such as S. typhimurium; or Serratia spp. such as S. marcescans. In a specific embodiment, a desired protein may be expressed in E. coli.

In addition to prokaryotic host cells, TNFbp(s) may be expressed in glycosylated form by any one of a number of suitable host cells derived from multicellular organisms. Such host cells are capable of complex processing and glycosylation activities. In principle, any higher eukaryotic cell culture might be used, whether such culture involves vertebrate or invertebrate cells, including plant and insect cells. Eukaryotic microbes such as filamentous fungi or yeast may be suitable hosts for the expression of a desired protein. Saccharomyces cerevisiae, or common baker's yeast, is the most commonly used among lower eukaryotic host microorganisms, but a number of other genera, species and strains are well known and commonly available.

Vertebrate cells may be used, as the propagation of vertebrate cells in culture (tissue culture) is a well-known procedure. Examples of useful mammalian host cell lines include, but are not limited to, monkey kidney CV1 line transformed by SV40 (COS-7), human embryonic kidney line (293 cells or 293 cells subcloned for growth in suspension culture), baby hamster kidney cells and Chinese hamster ovary cells. Other suitable mammalian cell lines include, but are not limited to, HeLa, mouse L-929 cells, 3T3 lines derived from Swiss, Balb-c or NIH mice, and BHK or HaK hamster cell lines. In a specific embodiment, a desired protein may be expressed in COS cells or in baculovirus cells.

A host cell may be transfected and preferably transformed with a desired nucleic acid under appropriate conditions permitting expression of the nucleic acid. The selection of suitable host cells and methods for transformation, culture, amplification, screening and product production and purification are well known in the art (Gething and Sambrook (1981), Nature, 293:620–625 or, alternatively, Kaufman et al. (1985), Mol. Cell. Biol., 5(7):1750–1759, or U.S. Pat. No. 4,419,446, the disclosures of which are hereby incorporated by reference). For example, for mammalian cells without cell walls, the calcium phosphate precipitation method may be used. Electroporation, micro-injection and other known techniques may also be used.

It is also possible that a desired protein may be produced by homologous recombination or with recombinant production methods utilizing control elements introduced into cells already containing DNA encoding a desired protein. Homologous recombination is a technique originally developed for targeting genes to induce or correct mutations in transcriptionally-active genes (Kucherlapati (1989), Prog. in Nucl. Acid Res. and Mol. Biol., 36:301, the disclosure of which is hereby incorporated by reference). The basic technique was developed as a method for introducing specific mutations into specific regions of the mammalian genome (Thomas et al. (1986), Cell, 44:419–428; Thomas and Capecchi (1987), Cell, 51:503–512 and Doetschman et al. (1988), Proc. Natl. Acad. Sci., 85:8583–8587, the disclosures of which are hereby incorporated by reference) or to correct specific mutations within defective genes (Doetschman et al. (1987), Nature, 330:576–578, the disclosure of which is hereby incorporated by reference). Exemplary techniques are described in U.S. Pat. No. 5,272,071; WO 92/01069; WO 93/03183; WO 94/12650 and WO 94/31560, the disclosures of which are hereby incorporated by reference.

Culturing the Host Cells

The method for culturing each of the one or more recombinant host cells for production will vary depending upon many factors and considerations; the optimum production procedure for a given situation will be apparent to those skilled in the art through minimal experimentation. Such recombinant host cells are cultured in a suitable media and the expressed protein is then optionally recovered, isolated and purified from the culture media (or from the cell, if expressed intracellularly) by appropriate means known to those skilled in the art.

Specifically, each of the recombinant cells used to produce a desired protein may be cultured in a culture media suitable for inducing promoters, selecting suitable recombinant host cells or amplifying the gene encoding the desired protein. The culture media may be supplemented as necessary with hormones and/or other growth factors (such as insulin, transferrin or epidermal growth factor), salts (such as sodium chloride, calcium, magnesium and phosphate), buffers (such as HEPES), nucleosides (such as adenosine and thymidine), antibiotics (such as gentamicin), trace elements (defined as inorganic compounds usually present at final concentrations in the micromolar range), and glucose or another energy source. Other supplements may also be included, at appropriate concentrations, as will be appreciated by those skilled in the art. Suitable culture conditions, such as temperature, pH and the like, are also well known to those skilled in the art for use with the selected host cells.

The resulting expression product may then be purified to near homogeneity by using procedures known in the art.

Exemplary purification techniques are taught in EP 393 438 and EP 422 339, the disclosures of which are hereby incorporated by reference.

Pharmaceutical Compositions

The present invention encompasses pharmaceutical preparations each containing therapeutically- or prophylactically-effective amounts of a TNFbp(s) or a chemically-modified derivative thereof (collectively, "TNFbp product(s)") in admixture with a vehicle. The vehicle preferably includes one or more pharmaceutically and physiologically acceptable formulation materials in admixture with the TNFbp product(s).

The primary solvent in a vehicle may be either aqueous or non-aqueous in nature. In addition, the vehicle may contain pharmaceutically acceptable excipients for modifying or maintaining the pH preferably between 5–6.5, and more preferably between 5.5–6.0 (e.g., buffers such as citrates or phosphates, and amino acids such glycine); viscosity; clarity; color; sterility; stability (e.g., sucrose and sorbitol); odor; rate of dissolution (e.g., solubilizers or solubilizing agents such as alcohols, polyethylene glycols and sodium chloride); rate of release; as well as bulking agents for lyophilized formulation (e.g., mannitol and glycine); surfactants (e.g., polysorbate 20, polysorbate 80, triton and pluronics); antioxidants (e.g., sodium sulfite and sodium hydrogen-sulfite); preservatives (e.g., benzoic acid and salicylic acid); flavoring and diluting agents; emulsifying agents; suspending agents; solvents; fillers; delivery vehicles and other pharmaceutical adjuvants and/or excipients. Other effective administration forms such as parenteral slow-release formulations, inhalant mists, orally-active formulations, or suppositories are also envisioned. The composition may also involve particulate preparations of polymeric compounds such as bulk erosion polymers (e.g., poly(lactic-co-glycolic acid) (PLGA) copolymers, PLGA polymer blends, block copolymers of PEG, and lactic and glycolic acid, poly(cyanoacrylates)); surface erosion polymers (e.g., poly(anhydrides) and poly(ortho esters)); hydrogel esters (e.g., pluronic polyols, poly(vinyl alcohol), poly (vinylpyrrolidone), maleic anhydride-alkyl vinyl ether copolymers, cellulose, hyaluronic acid derivatives, alginate, collagen, gelatin, albumin, and starches and dextrans) and composition systems thereof; or preparations of liposomes or microspheres. Such compositions may influence the physical state, stability, rate of in vivo release, and rate of in vivo clearance of the present proteins and derivatives. The optimal pharmaceutical formulation for a desired protein will be determined by one skilled in the art depending upon the route of administration and desired dosage. Exemplary pharmaceutical compositions are disclosed in *Remington's Pharmaceutical Sciences*, 18th Ed. (1990), Mack Publishing Co., Easton, Pa. 18042, pages 1435– 1712; Gombotz and Pettit (1995), *Bioconjugate Chem.*, 6:332–351; Leone-Bay, et al. (1995), *Journal of Medicinal Chemistry*, 38:4263–4269; Haas, et al. (1995), *Clinical Immunology and Immunopathology*, 76(1):93; WO 94/06457; WO 94/21275; FR 2706772 and WO 94/21235, the disclosures of which are incorporated herein by reference.

Specific sustained release compositions are available from the following suppliers: Depotech (Depofoam™, a multivesicular liposome) and Alkermes (ProLease™, a PLGA microsphere). Exemplary forms of hyaluronan are disclosed in Peyron and Balazs (1974), *Path. Biol.*, 22(8):731–736; Isdale et al. (1991), *J. Drug Dev.*, 4(2):93–99; Larsen et al. (1993), *Journal of Biomedical Materials Research*, 27:1129–1134; Namiki, et al. (1982), *International Journal of Clinical Pharmacology, Therapy and Toxicology*, 20(11):501–507; Meyer et al. (1995), *Journal of Controlled Release*, 35:67–72; Kikuchi et al. (1996), *Osteoarthritis and Cartilage*, 4:99–110; Sakakibara et al. (1994), *Clinical Orthopaedics and Related Research*, 299:282–292; Meyers and Brandt (1995), 22(9):1732–1739; Laurent et al. (1995), *Acta Orthop Scand*, 66(266):116–120; Cascone et al. (1995), *Biomaterials*, 16(7):569–574; Yerashalmi et al. (1994), *Archives of Biochemistry and Biophysics*, 313(2):267–273; Bernatchez et al. (1993), *Journal of Biomedical Materials Research*, 27(5):677–681; Tan et al. (1990), *Australian Journal of Biotechnology*, 4(1):38–43; Gombotz and Pettit (1995), *Bioconjugate Chem.*, 6:332–351; U.S. Pat. Nos. 4,582,865, 4,605,691, 4,636,524, 4,713,448, 4,716,154, 4,716,224, 4,772,419, 4,851,521, 4,957,774, 4,863,907, 5,128,326, 5,202,431, 5,336,767, 5,356,883; European Patent Application Nos. 0 507 604 A2 and 0 718 312 A2; and WO 96/05845, the disclosures of which are hereby incorporated by reference. Specific hyaluronan compositions are available from the following suppliers: BioMatrix, Inc. Ridgefield, N.J. (Synvisc™, a 90:10 mixture of a hylan fluid and hylan gel); Fidia S.p.A., Abano Terme, Italy (Hyalgan™, the sodium salt of a rooster comb-derived hyaluronic acid (~500,000 to ~700,000 MW)); Kaken Pharmaceutical Co., Ltd., Tokyo, Japan (Artz™, a 1% solution of a rooster-comb derived hyaluronic acid, ~700,000 MW); Pharmacia AB, Stockholm, Sweden (Healon™, a rooster-comb derived hyaluronic acid, ~4×10$^6$ MW); Genzyme Corporation, Cambridge, Mass. (Surgicoat™, a recombinant hyaluronic acid); Pronova Biopolymer, Inc. Portsmouth, N.H. (Hyaluronic Acid FCH, a high molecular weight (e.g., ~1.5–2.2×10$^6$ MW) hyaluronic acid prepared from cultures of *Streptococcus zooepidemicus*; Sodium Hyaluronate MV, ~1.0–1.6×10$^6$ MW and Sodium Hyaluronate LV, ~1.5–2.2×10$^6$ MW); Calbiochem-Novabiochem AB, Lautelfingen, Switzerland (Hyaluronic Acid, sodium salt (1997 company catalog number 385908) prepared from Streptococcus sp.); Intergen Company, Purchase, N.Y. (a rooster-comb derived hyaluronic acid, >1×10$^6$ MW); Diosynth Inc., Chicago, Ill.; Amerchol Corp., Edison, N.J. and Kyowa Hakko Kogyo Co., Ltd., Tokyo, Japan.

Once the pharmaceutical composition has been formulated, it may be stored in sterile vials as a solution, suspension, gel, emulsion, solid, or a dehydrated or lyophilized powder. Such compositions each may be stored either in a ready-to-use form or in a form (e.g., lyophilized) requiring reconstitution prior to administration. In a specific embodiment, the present invention is directed to kits for producing a single-dose administration unit. The kits may each contain both a first container having a dried protein and a second container having an aqueous formulation. Kits included within the scope of this invention are single and multi-chambered pre-filled syringes; exemplary pre-filled syringes (e.g., liquid syringes, and lyosyringes such as Lyo-Ject®, a dual-chamber pre-filled lyosyringe) are available from Vetter GmbH, Ravensburg, Germany.

Uses

TNFbp product(s) may be useful as research reagents and as therapeutic and diagnostic agents. Thus the TNFbp product(s) may be used in in vitro and/or in vivo diagnostic assays to quantify the amount of native TNFR-I, sTNFR-I, TNFR-II or sTNFR-II in a tissue or organ sample or to determine and/or isolate cells which express TNF (Scallon et al. (1995), supra). In assays of tissues or organs there will be less radioactivity from an $^{125}$I-TNFbp product(s) binding to TNF, as compared to a standardized binding curve of an $^{125}$I-TNFbp product(s), due to unlabeled native sTNFR-I or sTNFR-II binding to TNF. Similarly, the use of an $^{125}$I-TNFbp product(s) may be used to detect the presence of TNF in various cell types.

This invention also contemplates the use of TNFbp product(s) in the generation of antibodies and the resultant antibodies (specifically including those which also bind to native sTNFR-I or sTNFR-II). Antibodies can be developed which bind to TNFbp product(s). One of ordinary skill in the art can use well-known published procedures to obtain monoclonal, polyclonal antibodies or recombinant antibodies which specifically recognize and bind to the various proteins encoded by the amino acid sequences of the present invention. Such antibodies may then be used to purify and characterize the native sTNFR-I and native sTNFR-II, or to quantify the number of TNFR-I or TNFR-II expressed on a cell surface.

The present invention also relates to methods for the treatment of certain diseases and medical conditions (many of which can be characterized as inflammatory diseases) that are mediated by TNF, as well as the related sequela and symptoms associated therewith. A non-exclusive list of acute and chronic TNF-mediated diseases includes but is not limited to the following: cachexia/anorexia; cancer (e.g., leukemias); chronic fatigue syndrome; depression; diabetes (e.g., juvenile onset Type 1 and diabetes mellitus); fibromyelgia or analgesia; graft versus host rejection; hyperalgesia; inflammatory bowel disease; ischemic, including cerebral ischemia (brain injury as a result of trauma, epilepsy, hemorrhage or stroke, each of which may lead to neurodegeneration); lung diseases (e.g., adult respiratory distress syndrome and pulmonary fibrosis); multiple sclerosis; neuroinflammatory diseases; ocular diseases; pain; pancreatitis; pulmonary fibrosis; reperfusion injury; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Lyme disease, staphylococcal-induced ("septic") arthritis, Sjögren's syndrome, rheumatic fever, polychondritis and polymyalgia rheumatica and giant cell arteritis); septic shock; side effects from radiation therapy; systemic lupus erythematous; temporal mandibular joint disease; thyroiditis; tissue transplantation or an inflammatory condition resulting from strain, sprain, cartilage damage, trauma, orthopedic surgery, infection or other disease process.

The TNFbp product(s) may be administered to a patient in therapeutically effective amounts for the prevention or treatment of TNF-mediated diseases, including rheumatic diseases. The term "patient" is intended to encompass animals (e.g., cats, dogs and horses) as well as humans.

TNFbp product(s) may be administered via topical, enteral or parenteral administration including, without limitation, infusion, intraarterial, intraarticular, intracapsular, intracardiac, intradermal, intramuscular, intraorbital, intrathecal, intravenous, intraperitoneal, intraspinal, intrasternal injection, intraventricular, subcutaneous, subcuticular, subcapsular, subarachnoid and transtracheal. TNFbp product(s) may also be administered via oral administration or be administered through mucus membranes, that is, buccally, intranasally, rectally or sublingually for systemic delivery.

It is preferred that TNFbp product(s) be administered via intraarticular, intramuscular, intravenous or subcutaneous injection. Additionally, TNFbp product(s) may be administered by continuous infusion (e.g., constant or intermittent implanted or external infusion flow-modulating devices) so as to continuously provide the desired level of TNFbp product(s) in the blood for the duration of the administration. This is may be accomplished by means of a mini-pump, such as an osmotic mini-pump. In these ways, one can be assured that the amount of drug is maintained at the desired level and one can take blood samples and monitor the amount of drug in the bloodstream. Various pumps are commercially available, for example, from suppliers such as MiniMed Inc., Sylmar, Calif. (e.g., MT507) and Alza Corp., Palo Alto, Calif. (e.g. Alzet osmotic pump, model 2MLI).

It is also contemplated that other modes of continuous or near-continuous dosing may be practiced. For example, chemical derivatization may result in sustained release forms of the protein which have the effect of continuous presence in the blood stream, in predictable amounts based on a determined dosage regimen.

Modes of using TNFbp product(s) for the treatment of TNF-mediated diseases, including rheumatic diseases (e.g., osteoarthritis, psoriatic arthritis and rheumatoid arthritis), are set forth in European Patent Application 567566, the teachings of which are hereby incorporated by reference. By way of example but not limitation, in one specific embodiment, TNFbp product(s) may be administered intraarticularly for the treatment of rheumatoid arthritis and osteoarthritis. By way of example but not limitation in another specific embodiment, TNFbp product(s) may be administered subcutaneously or intramuscularly for the treatment of rheumatoid arthritis, inflammatory bowel disease, cachexia/anorexia or multiple sclerosis. By way of example but not limitation, in a still further specific embodiment TNFbp product(s) may be administered intravenously for the treatment of brain injury as a result of trauma, epilepsy, hemorrhage or stroke; or administered intraventricularly for the treatment of brain injury as a result of trauma. A specific mode for the treatment of arthritis includes: (1) a single intraarticular injection of a TNFbp product(s) given periodically as needed to prevent or remedy the flare-up of arthritis and (2) periodic subcutaneous injections of TNFbp product(s). In another specific embodiment, a TNFbp product(s) may be administered in the treatment of septic shock. The initiation of treatment for septic shock should begin as soon as possible after septicemia or the chance of septicemia is diagnosed. For example, treatment may be begun immediately following surgery or an accident or any other event that may carry the risk of initiating septic shock. Preferred modes for the treatment of adult respiratory distress syndrome include: (1) single or multiple intratracheal administrations of a TNFbp product(s) and (2) bolus or continuous intravenous infusion of a TNFbp product(s).

In another embodiment, cell therapy is also contemplated, e.g., implantation of cells producing a TNFbp product(s). This embodiment of the present invention may include implanting into patients cells which are capable of synthesizing and secreting a TNFbp product(s). Such cells producing a TNFbp product(s) may be cells which do not normally produce a TNFbp product(s) but which have been modified to produce a TNFbp product(s). The cells also may be cells whose ability to produce a TNFbp product(s) have been augmented by transformation with a polynucleotide suitable for the expression and secretion of a TNFbp product(s). In order to minimize a potential immunological reaction in patients by administering a TNFbp product(s) of a foreign species, it is preferred that the cells be of the same species as the patient (e.g., human) or that the cells be encapsulated with material that provides a barrier against immune recognition, or that cells be placed into an immunologically privileged anatomical location, such as in the testis, eye or central nervous system.

Human or non-human animal cells may be implanted into patients in biocompatible, semi-permeable polymeric enclosures or membranes to allow release of a TNFbp product(s), but to prevent destruction of the cells by the patient's immune system or by other detrimental factors from the surrounding tissue. Alternatively, the patient's own cells, transformed ex vivo to produce a TNFbp product(s), may be implanted directly into the patient without such encapsulation. The methodology for the membrane encapsulation of living cells is familiar to those of ordinary skill in the art, and the preparation of the encapsulated cells and their implantation in patients may be accomplished.

In yet another embodiment, in vivo gene therapy is also envisioned, wherein a nucleic acid sequence encoding a TNFbp product(s) is introduced directly into a patient. For example, a nucleic acid sequence encoding a TNFbp product (s) is introduced into target cells via local injection of a nucleic acid construct, with or without an appropriate delivery vector, such as an adeno-associated virus vector. Alternative viral vectors include but are not limited to retrovirus, adenovirus, herpes simplex virus and papilloma virus vectors. Physical transfer may be achieved in vivo by local injection of the desired nucleic acid construct or other appropriate delivery vector containing the desired nucleic acid sequence, liposome-mediated transfer, direct injection (naked DNA), receptor-mediated transfer (ligand-DNA complex) or microparticle bombardment (gene gun).

Exemplary cell and gene therapy techniques are disclosed in U.S. Pat. Nos. 4,892,538; 5,011,472; 5,106,627; DE 4219626, WO 94/20517 and 96/22793, the disclosures of which are hereby incorporated by reference.

Regardless of the manner of administration, the treatment of a TNF-mediated disease requires a dose or total dose regimen of a TNFbp product(s) effective to reduce or alleviate symptoms of the disease. Factors in determining the appropriate dosage or total dose regimen can include the disease or condition to be treated or prevented, the severity of the disease, the route of administration, and the age, sex and medical condition of the patient.

Further refinement of the calculations necessary to determine the appropriate dosage for treatment is routinely made by those skilled in the art, especially in light of the dosage information and assays disclosed herein. The frequency of dosing also depends on the pharmacokinetic parameters of the TNFbp product(s) in the formulation used. The TNFbp product(s) may be administered once, or in cases of severe and prolonged disorders, administered daily in less frequent doses or administered with an initial bolus dose followed by a continuous dose or sustained delivery. It is also contemplated that other modes of continuous or near-continuous dosing may be practiced. For example, chemical derivatization may result in sustained release forms which have the effect of a continuous presence in the bloodstream, in predictable amounts based on a determined dosage or total dosage regimen. The dosage or total dose regimen can also be determined through the use of known assays for determining dosages used in conjunction with appropriate dose-response data.

When administered parenterally, each unit dose, for example, may be up to 10 mg, generally up to 15 mg and more generally up to 20 mg. When administered into an articular cavity, the pharmaceutical composition is preferably administered as a single injection from, for example, a 3 to 10 ml syringe containing a dose, for example, of between about 5 mg/ml to 10 mg/ml TNFbp product(s) dissolved in isotonic phosphate buffered saline. The preparation may be administered into an articular cavity at a frequency, for example, of once every 7 to 10 days. In such a manner, the administration is continuously conducted, for example, 4 to 5 times while varying the dose if necessary.

As contemplated by the present invention, a TNFbp product(s) may be administered as an adjunct to other therapy and also with other pharmaceutical formulations suitable for the indication being treated. A TNFbp product(s) and any of one or more additional therapies or pharmaceutical formulations may be administered separately or in combination.

In a specific embodiment, the present invention is directed to the use of a TNFbp product(s) in combination (pretreatment, post-treatment or concurrent treatment) with one or more additional TNF inhibitors for the treatment of TNF-mediated diseases, including acute and chronic inflammation. TNF inhibitors include compounds and proteins which block in vivo synthesis or extracellular release of TNF, including the following compounds.

Additional TNF inhibitors include anti-TNF antibodies (e.g., MAK 195F Fab antibody (Holler et al. (1993), 1st International Symposium on Cytokines in Bone Marrow Transplantation, 147; CDP 571 anti-TNF monoclonal antibody (Rankin et al. (1995), *British Journal of Rheumatology*, 34:334–342, the disclosure of which is incorporated by reference); BAY X 1351 murine anti-tumor necrosis factor monoclonal antibody (Kieft et al. (1995), 7th European Congress of Clinical Microbiology and Infectious Diseases, 9, the disclosure of which is incorporated by reference); CenTNF cA2 anti-TNF monoclonal antibody (Elliott et al. (1994), *Lancet*, 344:1125–1127 and Elliott et al. (1994), *Lancet*, 344:1105–1110, the disclosures of which are incorporated by reference).

In a specific embodiment, the present invention is directed to the use of a TNFbp product(s) in combination (pretreatment, post-treatment or concurrent treatment) with secreted or soluble human fas antigen or recombinant versions thereof (WO 96/20206 and Mountz et al., *J. Immunology*, 155:4829–4837; and EP 510 691, the disclosures of which are hereby incorporated by reference). WO 96/20206 discloses secreted human fas antigen (native and recombinant, including an Ig fusion protein), methods for isolating the genes responsible for coding the soluble recombinant human fas antigen, methods for cloning the gene in suitable vectors and cell types, and methods for expressing the gene to produce the inhibitors. EP 510 691 teaches DNAs coding for human fas antigen, including soluble fas antigen, vectors expressing for said DNAs and transformants transfected with the vector. When administered parenterally, doses of a secreted or soluble fas antigen fusion protein each are generally from about 1 micrograms/kg to about 100 micrograms/kg.

In a specific embodiment, the present invention is directed to the use of a TNFbp product(s) in combination (pretreatment, post-treatment or concurrent treatment) with any of one or more interleukin-1 inhibitors for the treatment of TNF-mediated diseases, including acute and chronic inflammation such as cachexia/anorexia; chronic fatigue syndrome, depression; diabetes (e.g., juvenile onset Type 1 and diabetes mellitus); fibromyelgia or analgesia; graft versus host rejection; hyperalgesia, inflammatory bowel disease; ischemic injury, including cerebral ischemia (e.g., brain injury as a result of trauma, epilepsy, hemorrhage or stroke, each of which may lead to neurodegeneration); lung diseases (e.g., ARDS and pulmonary fibrosis); multiple sclerosis, ocular diseases; pain; pancreatitis, reperfusion injury; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Lyme disease, staphylococcal-induced ("septic") arthritis, Sjögren's syndrome, rheumatic fever, polychondritis and polymyalgia rheumatica and giant cell arteritis); septic shock; side effects from radiation therapy; temporal mandibular joint disease; tumor metastasis; or an inflammatory condition resulting from strain, sprain, cartilage damage, trauma, orthopedic surgery, infection or other disease processes. Classes of interleukin-1 inhibitors include interleukin-1 receptor antagonists (any compound capable of specifically preventing activation of cellular receptors to IL-1) such as IL-1ra, as described below; anti-IL-1 receptor monoclonal antibodies (e.g., EP 623674), the disclosure of which is hereby incorporated by reference; IL-1 binding proteins such as soluble IL-1 receptors (e.g., U.S. Pat. Nos. 5,492,888, 5,488, 032, and 5,464,937, 5,319,071, and 5,180,812, the disclosures of which are hereby incorporated by reference); anti-IL-1 monoclonal antibodies (e.g., WO 9501997, WO 9402627, WO 9006371, U.S. Pat. No. 4,935,343, EP 364778, EP 267611 and EP 220063, the disclosures of which are hereby incorporated by reference); IL-1 receptor accessory proteins (e.g., WO 96/23067, the disclosure of which is hereby incorporated by reference), and other compounds and proteins which block in vivo synthesis or extracellular release of IL-1.

Interleukin-1 receptor antagonist (IL-1ra) is a human protein that acts as a natural inhibitor of interleukin-1. Preferred receptor antagonists, as well as methods of making and methods of using thereof, are described in U.S. Pat. No. 5,075,222; WO 91/08285; WO 91/17184; AU 9173636; WO 92/16221; WO93/21946; WO 94/06457; WO 94/21275; FR 2706772; WO 94/21235; DE 4219626; WO 94/20517; WO 96/22793 and WO 97/28828 the disclosures of which are incorporated herein by reference. The proteins include glycosylated as well as non-glycosylated IL-1 receptor antagonists.

Specifically, three preferred forms of IL-1ra (IL-1raα, IL-1raβ and IL-1rax), each being derived from the same DNA coding sequence, are disclosed and described in U.S. Pat. No. 5,075,222. Methods for producing IL-1 inhibitors, particularly IL-1ras, are also disclosed in the 5,075,222 patent. In a specific embodiment, an IL-1ra contains an N-terminal methionyl group as a consequence of expression in E. coli. The present invention also includes modified IL-1ras. The modified IL-1ras include, for example, muteins of such inhibitors in which a cysteine residue is substituted for an amino acid at one or more sites in the amino acid sequence of a naturally-occurring inhibitor. Such muteins may then be site-selectively reacted with functionalized polyethylene glycol (PEG) units or other sulfhydryl-containing polyethers to create IL-1ra PEG species. WO 92/16221 discloses a number of modified IL-1ra species and methods of making such PEG modified inhibitors.

An additional class of interleukin-1 inhibitors includes compounds capable of specifically prventing activation of cellular receptors to IL-1. Such compounds include IL-1 binding proteins, such as soluble receptors and monoclonal antibodies. Such compounds also include monoclonal antibodies to the receptors.

A further class of interleukin-1 inhibitors includes compounds and proteins which block in vivo synthesis and/or extracellular release of IL-1. Such compounds include agents which affect transcription of IL-1 genes or processing of IL-1 preproteins.

Present treatment of TNF-mediated diseases, including acute and chronic inflammation such as rheumatic diseases includes the use of first line drugs for control of pain and inflammation classified as non-steroidal, anti-inflammatory drugs (NSAIDs). Secondary treatments include corticosteroids, slow acting antirheumatic drugs (SAARDs) or disease modifying (DM) drugs. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

In a specific embodiment, the present invention is directed to the use of a TNFbp product(s) and any of one or more NSAIDs for the treatment of TNF-mediated diseases, including acute and chronic inflammation such as rheumatic diseases and graft versus host disease. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In a more specific embodiment, the present invention is directed to the use of a TNFbp product(s) in combination (pretreatment, post-treatment or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate and sulfasalazine. Structurally related salicylic acid derivatives having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more propionic acid derivatives, prodrug esters or pharmaceutically acceptable salts thereof. The propionic acid derivatives, prodrug esters and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more acetic acid derivatives, prodrug esters or pharmaceutically acceptable salts thereof. The acetic acid derivatives, prodrug esters and pharmaceutically acceptable salts thereof comprise: acemetacin, alclofenac, amfenac, bufexamac, cinmetacin, clopirac, delmetacin, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, zidometacin and zomepirac. Structurally related acetic acid derivatives having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefanamic acid, niflumic acid, talniflumate, terofenamate, tolfenamic acid and ufenamate. Structurally related fenamic acid derivatives having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more carboxylic acid derivatives, prodrug esters or pharmaceutically acceptable salts thereof. The carboxylic acid derivatives, prodrug esters and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more butyric acid derivatives, prodrug esters or pharmaceutically acceptable salts thereof. The butyric acid derivatives, prodrug esters and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more oxicams, prodrug esters or pharmaceutically acceptable salts thereof. The oxicams, prodrug esters and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more pyrazoles, prodrug esters or pharmaceutically acceptable salts thereof. The pyrazoles, prodrug esters and pharmaceutically acceptable salts thereof which may be used comprise: difenamizole and epirizole. Structurally related pyrazoles having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more pyrazolones, prodrug esters or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more of the following NSAIDs: ∈-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprolm, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In a more specific embodiment, the present invention is directed to the use of a TNFbp product(s) in combination (pretreatment, post-treatment or concurrent treatment) with any of one or more corticosteroids, prodrug esters or pharmaceutically acceptable salts thereof for the treatment of TNF-mediated diseases, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more slow-acting antirheumatic drugs (SAARDs) or disease modifying antirheumatic drugs (DMARDS), prodrug esters or pharmaceutically acceptable salts thereof for the treatment of TNF-mediated diseases, including acute and chronic inflammation such as rheumatic diseases, graft versus host and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more COX2 inhibitors, prodrug esters or pharmaceutically acceptable salts thereof for the treatment of TNF-mediated diseases, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more antimicrobials, prodrug esters or pharmaceutically acceptable salts thereof for the treatment of TNF-mediated diseases, including acute and chronic inflammation. Antimicrobials include, for example, ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillan, erythromycin, flucloxacillan, gentamicin, gramicidin, methicillan, neomycin, oxacillan, penicillin and vancomycin. Structurally related antimicrobials having similar analgesic and anti-inflammatory properties are also intended to be encompassed by this group.

In a more specific embodiment, the present invention is directed to the use of a TNFbp product(s) in combination (pretreatment, post-treatment or concurrent treatment) with any of one or more of the following compounds for the treatment of TNF-mediated diseases, including acute and chronic inflammation: granulocyte colony stimulating factor; thalidomide; BN 50730; tenidap; E 5531; tiapafant PCA 4248; nimesulide; panavir; rolipram; RP 73401; peptide T; MDL 201,449A; (1R,3S)-Cis-1-[9-(2,6-diaminopurinyl)]-3-hydroxy-4-cyclopentene hydrochloride; (1R,3R)-trans-1-[9-(2,6-diamino)purine]-3-acetoxycyclopentane; (1R,3R)-trans-1-[9-adenyl)-3-azidocyclopentane hydrochloride and (1R,3R)-trans-1-[6-hydroxy-purin-9-yl)-3-azidocyclopentane.

It is especially advantageous to formulate compositions of the additional anti-inflammatory compounds in dosage unit form for ease of administration and uniformity of dosage. "Dosage unit form" as used herein refers to physically discrete units suited as unitary dosages for the patients to be treated, each unit containing a predetermined quantity of additional anti-inflammatory compounds calculated to produce the desired therapeutic effect in association with the required pharmaceutical carrier.

As used herein, "pharmaceutically acceptable carrier" includes any and all solvents, dispersion media, coating, antibacterial and antifungal agents, isotonic and absorption delaying agents and the like which are compatible with the active ingredient and with the mode of administration and other ingredients of the formulation and not deleterious to the recipient.

For oral therapeutic administration, the additional anti-inflammatory compound may be incorporated with excipients and used in the form of ingestible tablets, buccal tablets, troches, capsules, elixers, suspensions, syrups, wafers and the like, or it may be incorporated directly with the food in the diet. The tablets, troches, pills, capsules and the like may also contain the following: a binder such as gum tragacanth, acacia, corn starch or gelatin; excipients such as dicalcium phosphate; a disintegrating agent such as corn starch, alginic acid and the like; a lubricant such as magnesium stearate; a sweetening agent such as sucrose, lactose or saccharin; or a flavoring agent such as peppermint, oil of wintergreen or cherry or orange flavoring. When the dosage unit form is a capsule, it may contain, in addition to material of the type described herein, a liquid carrier. Various other materials may be present as a coating or to otherwise modify the physical form of the dosage unit. For instance, tablets, pills or capsules may be coated with shellac, sugar or both. Of course, any material used in preparing any dosage unit form should be pharmaceutically pure and substantially non-toxic in the amounts employed. In addition, the additional anti-inflammatory compound may be incorporated into a sustained-release preparation and formulation. The amount of the additional anti-inflammatory compound in such therapeutically useful composition is such that a suitable dosage will be obtained.

For parenteral therapeutic administration, each additional anti-inflammatory compound may be incorporated with a sterile injectable solution. The sterile injectable solution may be prepared by incorporating the additional anti-inflammatory compound in the required amount in an appropriate pharmaceutically acceptable carrier, with various other ingredients, followed by filtered sterilization. In the case of dispersions, each may be prepared by incorporating the additional anti-inflammatory compound into a sterile vehicle which contains the basic dispersion medium and the required other ingredients from those enumerated herein. In the case of sterile injectable solutions, each may be prepared by incorporating a powder of the additional anti-inflammatory compound and, optionally, any additional desired ingredient from a previously sterile-filtered solution thereof, wherein the powder is prepared by any suitable technique (e.g., vacuum drying and freeze drying).

The use of such media and agents is well known in the art (see for example, *Remington's Pharmaceutical Sciences*, 18th Ed. (1990), Mack Publishing Co., Easton, Pa. 18042, pages 1435–1712, the disclosure of which is hereby incorporated by reference). Supplementary active ingredients can also be incorporated into the compositions.

The specific dose of the additional anti-inflammatory compound is calculated according to the approximate body weight or surface area of the patient. Other factors in determining the appropriate dosage can include the acute and chronic inflammatory disease or condition to be treated or prevented, the severity of the disease, the route of administration and the age, sex and medical condition of the patient. Further refinement of the calculations necessary to determine the appropriate dosage for treatment involving each of the herein-mentioned formulations is routinely made by those skilled in the art. Dosages can also be determined through the use of known assays for determining dosages used in conjunction with appropriate dose-response data.

Thus, for example, it is within the scope of the invention that doses of the additional anti-inflammatory compounds selected for treating a particular acute or chronic inflammatory disease such as rheumatic diseases can be varied to achieve a desired therapeutic effect. Where one of the additional anti-inflammatory compounds has side effects, it can be given to patients during alternate treatment periods of combination therapy. For example, chronic methotrexate treatment is associated with gastrointestinal, hepatic, bone marrow and pulmonary toxicity (Sandoval et al. (1995), *British Journal of Rheumatology*, 34:49–56, the disclosure of which is hereby incorporated by reference).

Tests for monitoring the improvement of a disease can include specific tests directed, for example, to the determination of systemic response to inflammation, which include the erythrocyte sedimentation rate (ESR) and acute phase reactants (APR). Observations are made of the swelling, etc. of the afflicted body parts. Improvement in stiffness, and grip (where applicable), and reduction in pain of the patient is also observed. If the patient's condition is stable, the patient is re-treated at the same dosage weekly and is evaluated weekly. Provided the patient's condition is stable, the treatment may be continued. After six months of treatment, anatomical changes of the skeleton are determined by radiologic imaging, for example by X-radiography.

At the end of each period, the patient is again evaluated. Comparison of the pre-treatment and post-treatment radiological assessment, ESR and APR indicates the efficacy of the treatments. According to the efficacy of the treatments and the patient's condition, the dosage may be increased or maintained constant for the duration of treatment.

Preferably, the present invention is directed to a method with, optionally, one of the following combinations to treat or prevent TNF-mediated diseases, including acute and chronic inflammation such as rheumatic diseases and the symptoms associated therewith. One combination is a TNFbp product(s) (e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1) thereof) with one or more of methotrexate, leflunomide, an immunosuppressant (e.g., cyclosporin), ciprofloxacin, secreted or soluble fas antigen and an IL-1 inhibitor (e.g., IL-1ra). Preferred combinations include the TNFbp product(s) and methotrexate, or the TNFbp product(s) and leflunomide. Another combination is a TNFbp product(s) (e.g., STNFR-I, sTNFR-II, sTNFR fragments (2.6 D sTNFRs such as 2.6 D sTNFR-I) or sTNFR Fc(s) (sTNFR-I/IgG1 or sTNFR-II/IgG1) thereof) with one or more of methotrexate, leflunomide, sulphasazine and hydroxychloroquine.

In a specific preferred embodiment, the method comprises the administration (e.g., intra-articular, subcutaneous or intramuscular) of TNFbp product(s) (e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination (pretreatment, post-treatment or concurrent treatment) with methotrexate and/or leflunomide and/or an IL-1 inhibitor (e.g., IL-1ra) and/or a secreted or soluble Fas antigen to treat rheumatic diseases.

In a specific preferred embodiment, the method comprises the administration (e.g., intravenous or intraventricular) of a TNFbp product(s) (e.g., sTNFR-I, sTNFR-II, STNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination (pretreatment, post-treatment or concurrent treatment) with tissue plasminogen activator and/or an IL-1 inhibitor (e.g. IL-1ra) to treat brain injury as a result of trauma, epilepsy, hemorrhage or stroke, each of which may lead to neurodegeneration.

In a specific preferred embodiment, the method comprises the administration (e.g., subcutaneous or intramuscular) of a TNFbp product(s) (e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination (pretreatment, post-treatment or concurrent treatment) with one or more of a corticosteroid, cyclosporin, FK-506, or an interferon (e.g., alpha interferon, beta interferon, gamma interferon or consensus interferon) and/or an IL-1 inhibitor (e.g. IL-1ra, optionally formulated with a controlled release polymer (e.g., a dextran or hyaluronan)) to treat multiple sclerosis.

In a specific preferred embodiment, the method comprises the administration (e.g., subcutaneous or intramuscular) of a TNFbp product(s) (e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination (pretreatment, post-treatment or concurrent treatment) with G-CSF and/or an IL-1 inhibitor (e.g. IL-1ra) to treat inflammatory bowel disease.

In a specific preferred embodiment, the method comprises the administration (e.g., subcutaneous or intramuscular) of a TNFbp product(s) (e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination (pretreatment, post-treatment or concurrent treatment) with leptin, Marinol® or Megace® to treat cachexia/anorexia.

In a specific preferred embodiment, the method comprises the administration (e.g., subcutaneous or intramuscular) of a TNFbp product(s) (e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination (pretreatment, post-treatment or concurrent treatment) with leptin to treat diabetes.

In a specific preferred embodiment, the method comprises the administration (e.g., subcutaneous, intraventricular or intrathecal) of a TNFbp product(s) (e.g., sTNFR-I, STNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination (pretreatment, post-treatment or concurrent treatment) with an NSAID (e.g., indomethacin) and/or an IL-1 inhibitor (e.g. IL-1ra) to treat Alzheimer's disease.

In a specific preferred embodiment, the method comprises the administration (e.g., subcutaneous, intraventricular or intrathecal) of a TNFbp product(s) (e.g., sTNFR-I, sTNFR-II, sTNFR fragments (2.6 D sTNFRs such as 2.6 D siNFR-I) or sTNFR Fc(s) (sTNFR-I/IgG1 or sTNFR-II/IgG1), optionally formulated with a controlled release polymer (e.g., a dextran or hyaluronan)) optionally in combination (pretreatment, post-treatment or concurrent treatment) with a secreted or soluble fas antigen to treat cancer (e.g., leukemias); diabetes (e.g., juvenile onset Type 1 diabetes mellitus); graft versus host rejection; hepatitis; ischemic/reperfusion injury, including cerebral ischemia (brain injury as a result of trauma, epilepsy, hemorrhage or stroke, each of which may lead to neurodegeneration); neuroinflammatory diseases; rheumatic diseases, and tissue transplantation.

In a specific preferred embodiment, the method comprises the administration (e.g., subcutaneous, intraventricular or intrathecal) of a TNFbp product(s) (e.g., STNFR-I, STNFR-II, STNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) optionally in combination (pretreatment, post-treatment or concurrent treatment) with osteoprotogerin (European Patent Application No. 96309363.8) in the treatment of osteoporosis or Paget's disease.

In a specific preferred embodiment, the method comprises the administration (e.g., subcutaneous, intraventricular or intrathecal) of a TNFbp product(s) ((e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) in combination with gene therapy (e.g., using the human adenovirus) to modulate the inflammatory response to vector antigens (Zhang et al. (1997), *Arthritis & Rheumatism,* 40(9) :S220 (1138)).

The surprising and unexpected result disclosed herein is the ability of TNFbp product(s) (e.g., sTNFR-I, sTNFR-II, sTNFR fragments (2.6 D sTNFRs such as 2.6 D sTNFR-I) or sTNFR Fc(s) (sTNFR-I/IgG1 or sTNFR-II/IgG1), optionally formulated with a controlled release polymer (e.g., a dextran or hyaluronan)) and methotrexate to act synergistically in the treatment of various symptoms associated with TNF-mediated diseases, including acute and chronic inflammation such as rheumatic diseases. "Synergistically]" is used herein to refer to a situation where the benefit conveyed by the joint administration of inhibitors is greater than the algebraic sum of the effects resulting from the separate administration of components of the combination. As shown in the experiments below, in the adjuvant arthritis model the combination treatment of TNFbp product(s) and methotrexate is synergistic with respect to treating systemic inflammation (i.e., splenomegaly) and weight loss associated with rheumatoid arthritis. Thus, the combined treatment with TNFbp product(s) and methotrexate has the advantage of achieving the same result with a lower dose or less frequent administration of methotrexate, thereby reducing any toxic effect and potentially the advantage of persisting even after the treatment has terminated.

Methotrexate is an anti-metabolite and immunosuppressive drug. Methotrexate is an effective anti-inflammatory agent with utility in the treatment of severe and disabling psoriasis and rheumatoid arthritis (Hoffmeister (1983), *The American Journal of Medicine,* 30:69–73 and Jaffe (1988), *Arthritis and Rheumatism,* 31:299). Methotrexate is N-[4-[(2,4-diamino-6-pteridinyl)methylamino]benzoyl]-L-glutamic acid and has the structural formula:

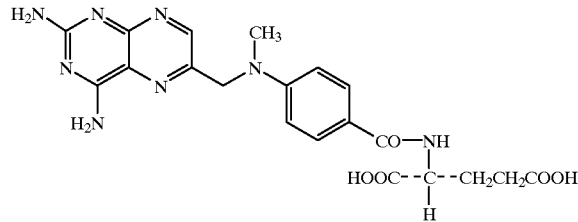

The following references describe the preparation of methotrexate (Seeger et al. (1949), *J. Am. Chem. Soc.,* 71:1753; the metabolism of methotrexate (Freeman (1958), *J. Pharmacol. Exp. Ther,* 122:154 and Henderson et al. (1965), *Cancer Res.,* 25:1008); the toxicity of methotrexate (Condit et al. (1960), *Cancer,* 13:222–249; the pharmacokinetic models of methotrexate (Bischoff et al. (1970), *J. Pharm, Sci.,* 59:149); the metabolism and pharmacokinetics of methotrexate (Evans (1980), *Appl. Pharmacokinet.,* Williams et al. (eds.), pp. 518–548 (Appl. Ther., Inc.); the clinical pharmacology of methotrexate (Bertino (1981), *Cancer Chemother.,* 3:359–375 and Jolivet et al. (1983), *N. Eng. J. Med.,* 309:1094–1104); and the clinical experience of methotrexate in rheumatoid arthritis (Weinblatt et al. (1985), *N. Eng. J. Med.,* 312:818–822; Furst (1985), *J. Rheumatol.,* 12(12) :1–14; Williams et al. (1985), *Arthritis Rheum.,* 28:721–730 and Seitz et al. (1995), *British Journal of Rheumatology,* 34:602–609). Additionally, numerous patents have been issued disclosing active agent methotrexate and methods for synthesizing methotrexate or potential intermediates in the synthesis of methotrexate: U.S. Pat. Nos. 2,512,572, 3,892,801, 3,989,703, 4,057,548, 4,067, 867, 4,079,056, 4,080,325, 4,136,101, 4,224,446, 4,306,064, 4,374,987, 4,421,913 and 4,767,859.

The mechanism of action of methotrexate is poorly understood, however various activities of this drug have been demonstrated which likely contribute to its efficacy (Segal et al. (1990), *Seminars in Arthritis and Rheumatism,* 20:190–198). The following mechanisms of action for methotrexate have been postulated: inhibition of folate-dependent pathways and protein metabolism (Morgan et al. (1987), *Arthritis and Rheumatism,* 30:1348–1356); inhibition of neutrophil migration into arthritic joints (Van de Kerkhof et al. (1985), *British Journal of Dermatology,* 113:251–255; Ternowitz et al. (1987), *Journal of Investigative Dermatology,* 89:192–196 and Sperling (1992), *Arthritis and Rheumatism,* 35:376–384); IL-6 inhibitory activity (Segal (1991), *Arthritis and Rheumatism,* 34(2):146–152) and the local specific anti-proliferative effect on cells involved in arthritis (Rodenhuis et al. (1987), *Arthritis and Rheumatism,* 30:369–374). Methotrexate has been shown to block the interleukin-1 beta/interleukin-1 receptor pathway (Brody et al. (1993), *European Journal of Clinical Chemistry and Clinical Biochemistry,* 31(10):667–674); however, although methotrexate may inhibit the proliferative effects of IL-1 and decrease monocyte IL-1 production in the short term in certain patients, this effect is not sustained and is unlikely to explain the long-term efficacy of methotrexate (Barrera et al. (1996), *Seminars in Arthritis and Rheumatism*, 25(4) :234–253).

Methotrexate may be administered orally, intraperitoneally, subcutaneously or intravenously. Oral administration is preferred. The following is an example of the procedure for the combined administration of a TNFbp product(s) and methotrexate to treat a human patient. The patient takes a tablet or capsule of methotrexate three times a week, at a total weekly dose of 5 to 50 mg/patient/week. The patient also is injected intravenously with TNFbp product(s), at a daily dose of 50 to 150 mg. It will be appreciated by those skilled in the art that the doses presented herein are the preferred doses. The starting dose of the particular compound(s) used is reduced for a patient who exhibits adverse reaction, or the drug used in combination with the compound(s) can be changed or reduced, e.g., depending on the different formulations, routes, dose schedules and/or other variables known to those skilled in the art, such as the individual patient's tolerance of the drug, its efficacy and toxicity.

Preferably, the patient is treated with a weekly starting dose of methotrexate at between 5 mg and 7.5 mg (orally or intramuscularly) and a daily dose of TNFbp product(s) at between 50 mg and 150 mg intravenously. The dosage of methotrexate is increased by 5 mg every 2 to 3 weeks. The maximum dosage level is determined at a point at which the patient shows improvements, which is generally preferably less than about 25 mg of methotrexate per week, more preferably between 5 to 25 mg of methotrexate per week. At the end of the five-day period the patient is evaluated. The evaluation includes physical examination and extensive laboratory testing. The tests include evaluation for toxicity. Additional laboratory monitoring in the case of methotrexate preferably includes a complete blood cell count every 2 weeks for the first 3 months and then monthly thereafter. Additional precautions preferably include monthly assessments of levels of serum albumin, alanine amino transferase, bilirubin, creatinine and blood urea nitrogen. Monthly urinalysis is also preferred.

The above is by way of example and does not preclude the treatment of other inflammatory joint diseases arising from abnormal or undesirably normal immune responses. The example also does not preclude other treatments to be used concurrently with these anti-inflammatory compounds that are known by those skilled in the art or that could be arrived at by those skilled in the art using the guidelines set forth in this specification. Other anti-inflammatory compounds mentioned above can be used in combination with the treatments.

EXAMPLES

Standard methods for many of the procedures described in the following examples, or suitable alternative procedures, are provided in widely recognized manuals of molecular biology such as, for example, Sambrook et al., *Molecular Cloning*, Second Edition, Cold Spring Harbor Laboratory Press (1987) and Ausabel et al., *Current Protocols in Molecular Biology*, Greene Publishing Associates/Wiley Interscience, New York (1990). All chemicals were either analytical grade or USP grade.

Example 1

An animal model of rheumatoid arthritis induced by an adjuvant was used to investigate the combination therapy of a TNF binding protein and methotrexate in male Lewis rats (3–7/group) weighing at least 200 g.

On day-0, all rats were injected with 100 µl of Freunds Complete Adjuvant (Sigma Chemical Co., St. Louis, Mo.) to which a synthetic adjuvant, N,N-dioctyldecyldecyl-N', N-bis(2-hydroxy-ethyl) propanediamine, 50 mg/ml, was added. On days 0–14 methotrexate in 1% carboxymethylcellulose (Sigma) was orally administered daily (0.06 mg/kg) to two groups of rats. On days 8, 10, 12, and 14, *E. coli*-derived c105 sTNFR-I dimerized with PEG-20,000-bis-vinyl sulfone (c105 sTNFR-I dumbbell; prepared generally in accordance with the teachings of WO 95/34326) formulated in pharmaceutical composition (34 mM NaCl, 10 mM sodium phosphate, 4% sorbitol (w/v) in water; pH 6.5) was administered by subcutaneous (SC) injection (3 mg/kg) to one group of rats being treated with both Freunds Complete Adjuvant and methotrexate and to another group of rats being treated with Freunds Complete Adjuvant alone.

Body weights were taken on day 0 and every other day from day 9 to termination on day 15. Caliper measurements and clinical scoring were done on day 9 and every other day until termination. At this time animal's body, paw and spleen weights were determined.

Figure 4:
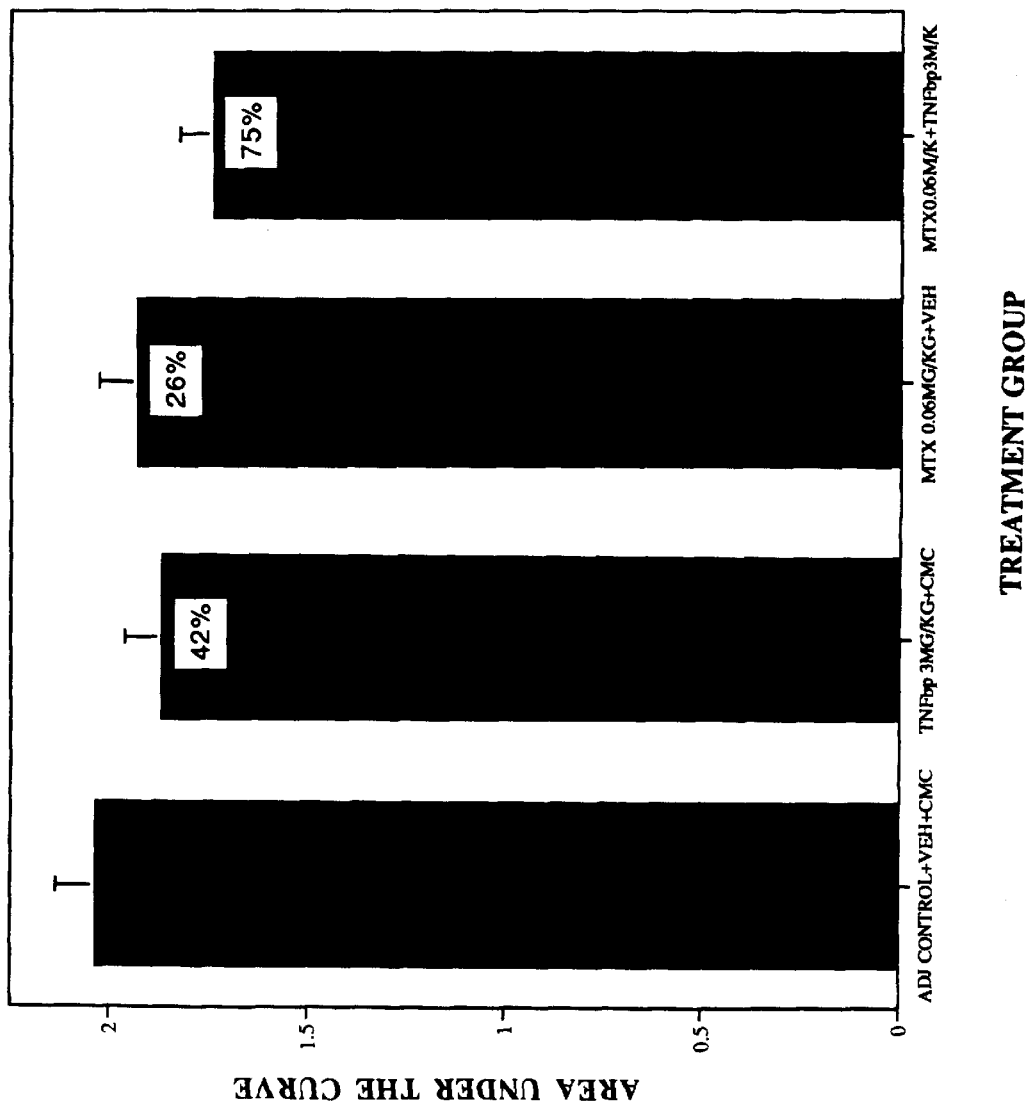
FIG. 4 depicts the effects of c105 sTNFR-I dumbbell alone, methotrexate alone and the combination of c105 sTNFR-I dumbbell and methotrexate on final paw weights (index of arthritis), splenomegaly (index of systemic inflammation) and body weight change in the adjuvant arthritic rats in Example 1.

As seen in FIGS. 3 and 4, rats treated with c105 sTNFR-I dumbbell alone exhibited about 42% inhibition of paw swelling (area under the curve—AUC), no significant benefit on splenomegaly (not shown) and about 13.2% inhibition of body weight change (not shown). Rats treated with methotrexate had 26% inhibition of paw swelling (AUC), no inhibition of spleen weight (not shown) and 3% inhibition of body weight change (not shown). The combination therapy provided 75% inhibition of paw swelling (AUC), 48% inhibition of splenomegaly (not shown) and 16.2% inhibition of body weight change (not shown).

Figure 5:
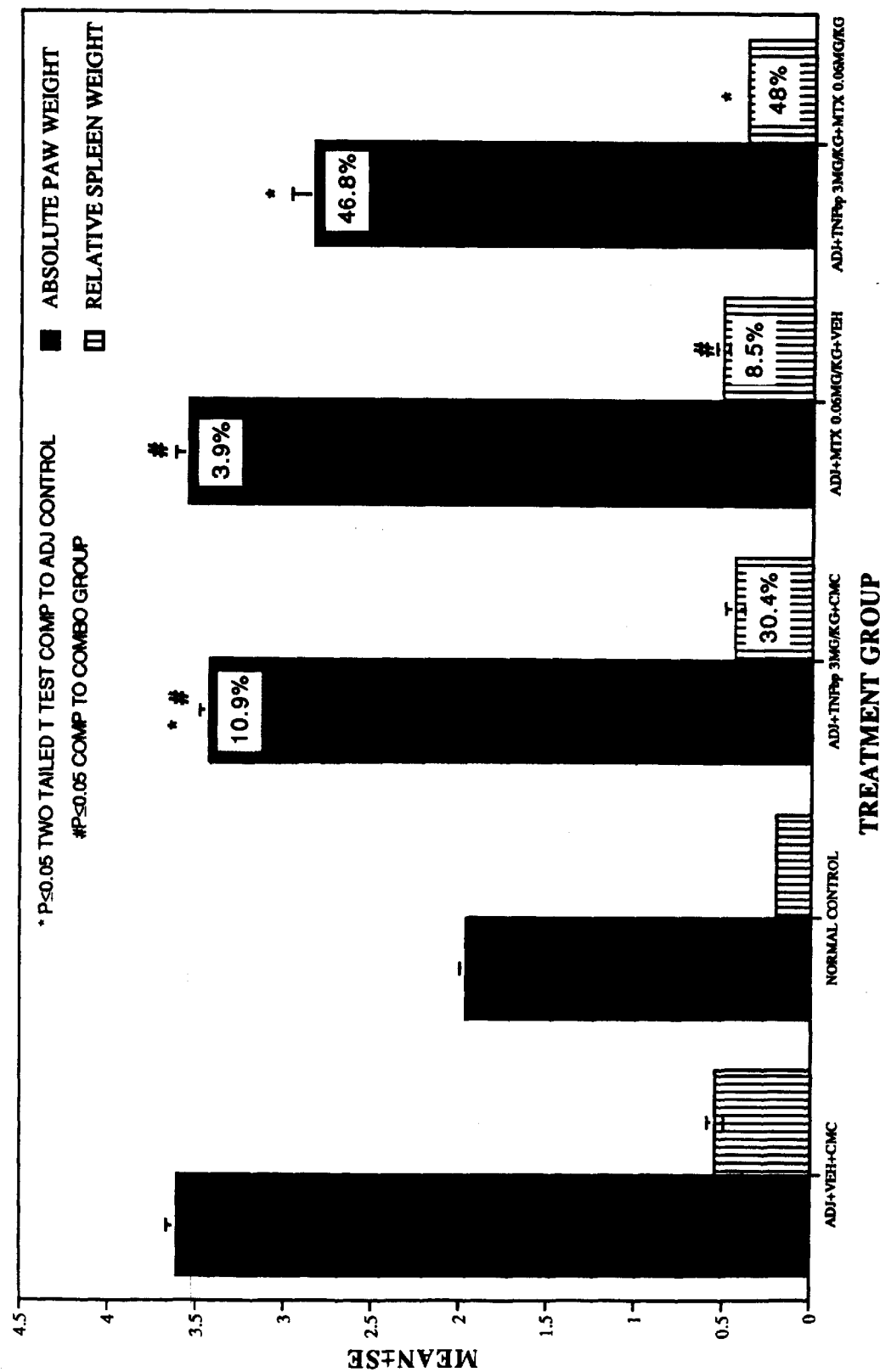
FIG. 5 depicts the final analysis (inhibition at termination) of the effects of c105 sTNFR-I dumbbell alone, methotrexate alone and the combination of c105 sTNFR-I dumbbell and methotrexate on joint diameter in the adjuvant arthritic rats in Example 1.

As seen in FIG. 5, the final analysis (inhibition at termination) of terminal paw weights and spleen weights indicated that c105 sTNFR-I dumbbell alone resulted in 10.9% inhibition of paw inflammation, 30.4% inhibition of splenomegaly and 13.2% inhibition of body weight change (not shown). Methotrexate treatment alone gave only a 3.9% inhibition of paw inflammation, 8.5% inhibition of splenomegaly and 3% inhibition of body weight change (not shown). The combination of c105 sTNFR-I dumbbell and methotrexate resulted in a 46.8% inhibition of paw swelling, 48% inhibition of splenomegaly and 16.2% inhibition of body weight change (not shown).

Example 2

An animal model of rheumatoid arthritis induced by an adjuvant was used to investigate the combination therapy of a TNF binding protein and methotrexate in male Lewis rats (5–7/group) weighing at least 200 g.

On day-0, all rats were injected with 100 µl of Freunds Complete Adjuvant (Sigma Chemical Co., St. Louis, Mo.) to which a synthetic adjuvant, N,N-dioctyldecyldecyl-N', N-bis(2-hydroxy-ethyl) propanediamine, 50 mg/ml, was added. On day 0–14 methotrexate in 1% carboxymethylcellulose (Sigma) was orally administered daily (0.06 mg/kg) to two groups of rats. On days 9, 11, and 13, CHO-derived sTNFR-II/hIgG1 fusion protein (sTNFR-II Fc; prepared generally in accordance with the teachings of EP 418 014) formulated in pharmaceutical composition (34 mM NaCl, 10 mM sodium phosphate, 4% sorbitol (w/v) in water; pH 6.5) was administered by subcutaneous infusion (18 mg/kg) to one group of rats being treated with both Freunds Complete Adjuvant and methotrexate and to another group of rats being treated with Freunds Complete Adjuvant alone.

Body weights were taken on day 0 and every other day from day 9 to termination on day 15. Caliper measurements and clinical scoring were done daily from day 9 until termination on day 15. At this time animal's body, paw and spleen weights were determined.

Figure 6:
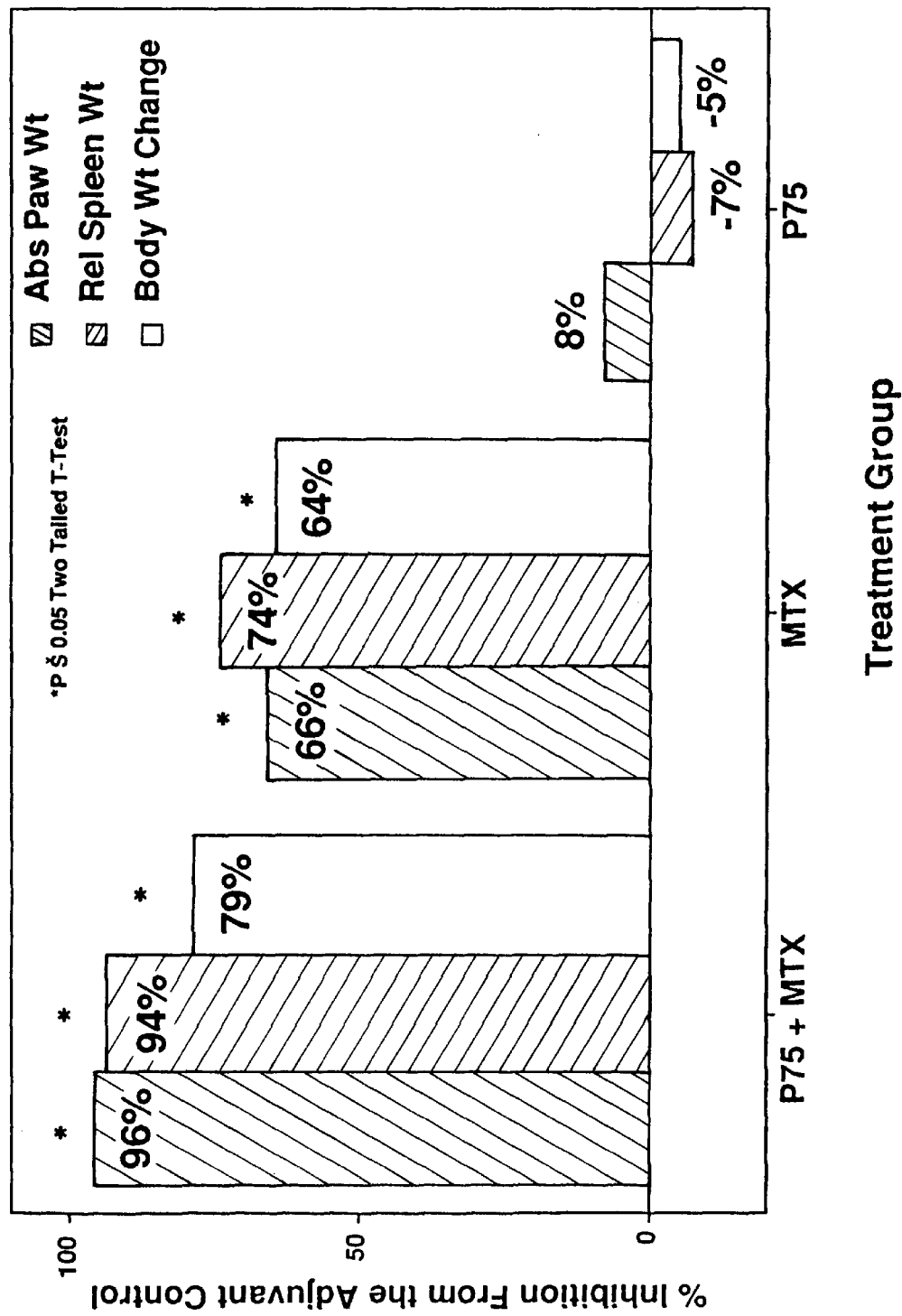
FIG. 6 depicts the effects of sTNFR-II/Fc alone, methotrexate alone and the combination of sTNFR-II/Fc with methotrexate on final paw weights (index of arthritis), splenomegaly (index of systemic inflammation) and body weight change in the adjuvant arthritic rats in Example 2.

As seen in FIG. 6, rats treated with sTNFR-II Fc alone exhibited about 8% inhibition of paw swelling (area under the curve—AUC), with no significant benefit on splenomegaly (−7%) or body weight change (−5%). Rats treated with methotrexate had 66% inhibition of paw swelling (AUC), 74% inhibition of spleen weight and 64% inhibition of body weight change. The combination therapy provided 96% inhibition of paw swelling (AUC), 94% inhibition of splenomegaly and 79% inhibition of body weight change.

Figure 7:
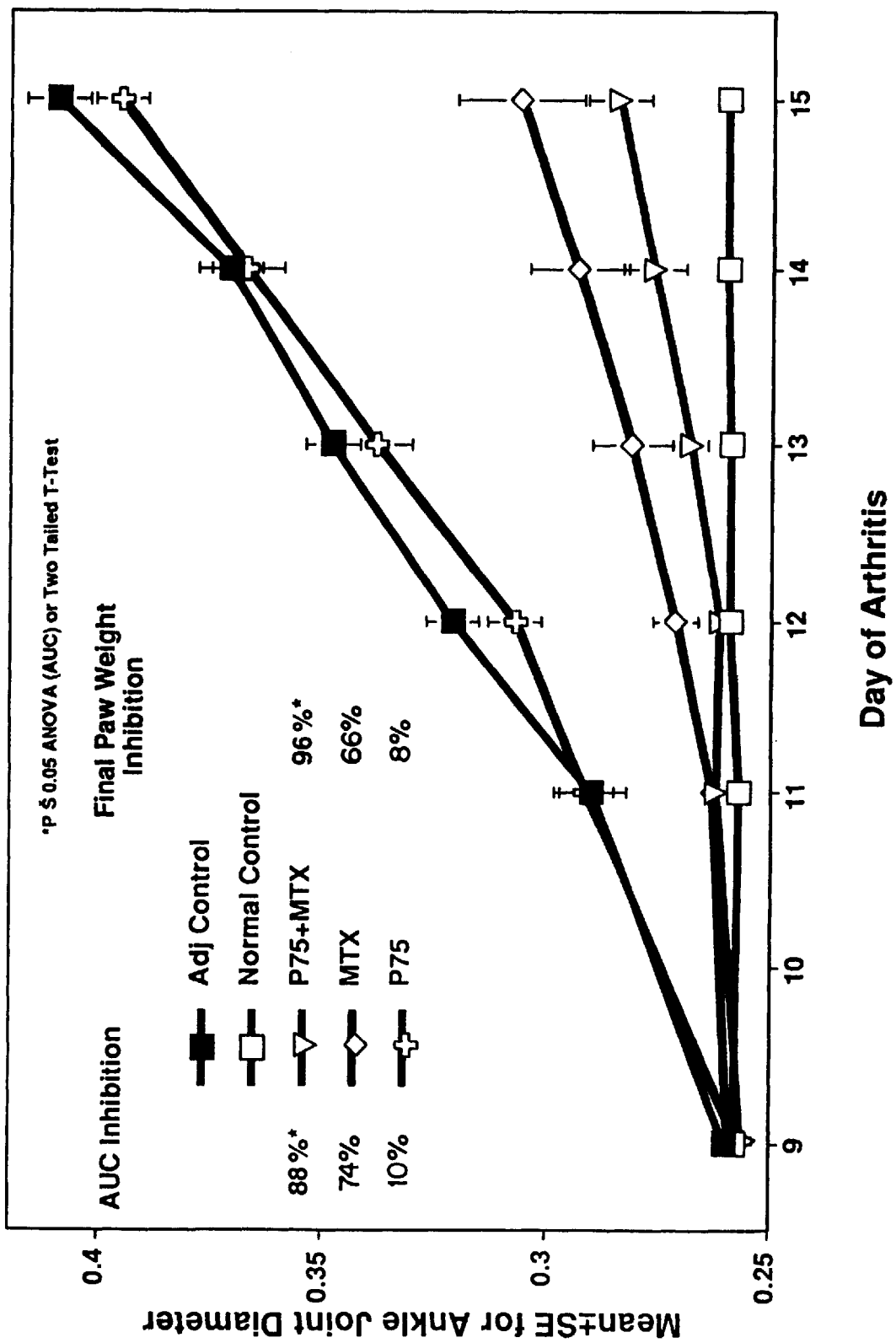
FIG. 7 depicts the effects of sTNFR-II/Fc alone, methotrexate alone and the combination of sTNFR-II/Fc with methotrexate on adjuvant arthritic rats in Example 2.

As seen in FIG. 7, the final analysis (inhibition at termination) of terminal paw weights indicated that sTNFR-II Fc alone resulted in 10% inhibition of paw inflammation, methotrexate treatment alone gave a 74% inhibition of paw inflammation and the combination of sTNFR-II Fc and methotrexate resulted in a 88% inhibition of paw swelling.

Example 3

The combination immunotherapeutic effects of c105 sTNFR-I dumbbell and fas fusion protein were assessed using a mouse model of D-Galactosamine (D-GalNH$_2$) induced lethality. The D-galactosamine (D-GalNH$_2$)/ Lipopolysaccharide (LPS) model (Mountz et al., *J. Immunology*, 155:4829–4837). In this model, MRL-lpr/lpr autoimmune mice are administered D-GalNH$_2$ with bacterial endotoxin (LPS), and lethality is observed through +96 hours post challenge.

Materials and Methods

Dihydrofolate reductase (DHFR) deficient Chinese hamster ovary cells (CHOd-cells) were transfected with fas/ hIgG1 chimeric cDNA (Mountz, et al. (1996), "Autoimmunity Due to Defective Nur-77, Fas and TNF-R1 Apoptosis" in Mechanisms of Lymphocyte Activation and Immune Regulation, Vol. 6, p241–262 (Gupta and Cohen (Eds)), Plenem Press, NY) in pDSRα2, generally in accordance with the disclosure of DeClerck, et al. (1991), *JCB*, 266:3893–3899. The transfection procedure differed from the protocol of set forth in DeClerck, et al. (1991), supra, as follows: the cells were transfected with 800,000 cells, with 10 micrograms and 8 micrograms of herring sperm as a carrier, and the cells were split at 2 days post-transfection.

Following expression of the fas fusion protein, the protein was purified using a Protein G Sepharose Fast Flow, generally in accordance with Jungbauer, et al. (1989), *J. Chrom.*, 476:257–268. The purified protein was formulated in Phosphate buffered saline (Gibco BRL, Grand Island, N.Y.).

Protocol

After overnight fasting, 6–8 week old female MRL-lpr/lpr mice (Jackson Laboratory, Bar Harbor, Me. (5/7/group) were cannulated with jugular catheters and allowed to recover for several days. They were then placed in infusion cages and acclimated for a week prior initiating saline infusion.

At hour-0, all mice were injected intraperitoneally with 31 micrograms of D-GalNH$_2$ (Sigma) suspended in Hank's Balanced Salt Solution (Gibco BRL) (120 micrograms/ml); and lipopolysaccharide (LPS) from *E. coli* Serotype 0127:B8 (Sigma) in sterile, endotoxin-free phosphate buffered saline (PBS) (6 micrograms/mouse).

At 0-hour-+2 hours post-challenge, fas fusion protein formulated in a pharmaceutical composition (Phosphate buffered saline (Gibco BRL, Grand Island, N.Y.)) was administered intravenously in serial 2-fold dilutions (microgram/kg dosages) to two groups of mice.

At 0-hour-+2 hours post-challenge, c105 sTNFR-I dumbbell formulated in a pharmaceutical composition (34 mM NaCl, 10 mM sodium phosphate, 4% sorbitol (w/v) in water; pH 6.5) was administered intravenously in serial 2-fold dilutions (microgram/kg dosages) to one group of mice being treated with both D GalNH$_2$ and fas fusion protein and to another group of mice being treated with D-GalNH$_2$ alone.

ED$_{50}$ curves were generated with statistical software for the MacIntosh (Statview®, Mountain View, Calif.). Lethality was followed through +96 hour after challenge.

Results

Figure 8:
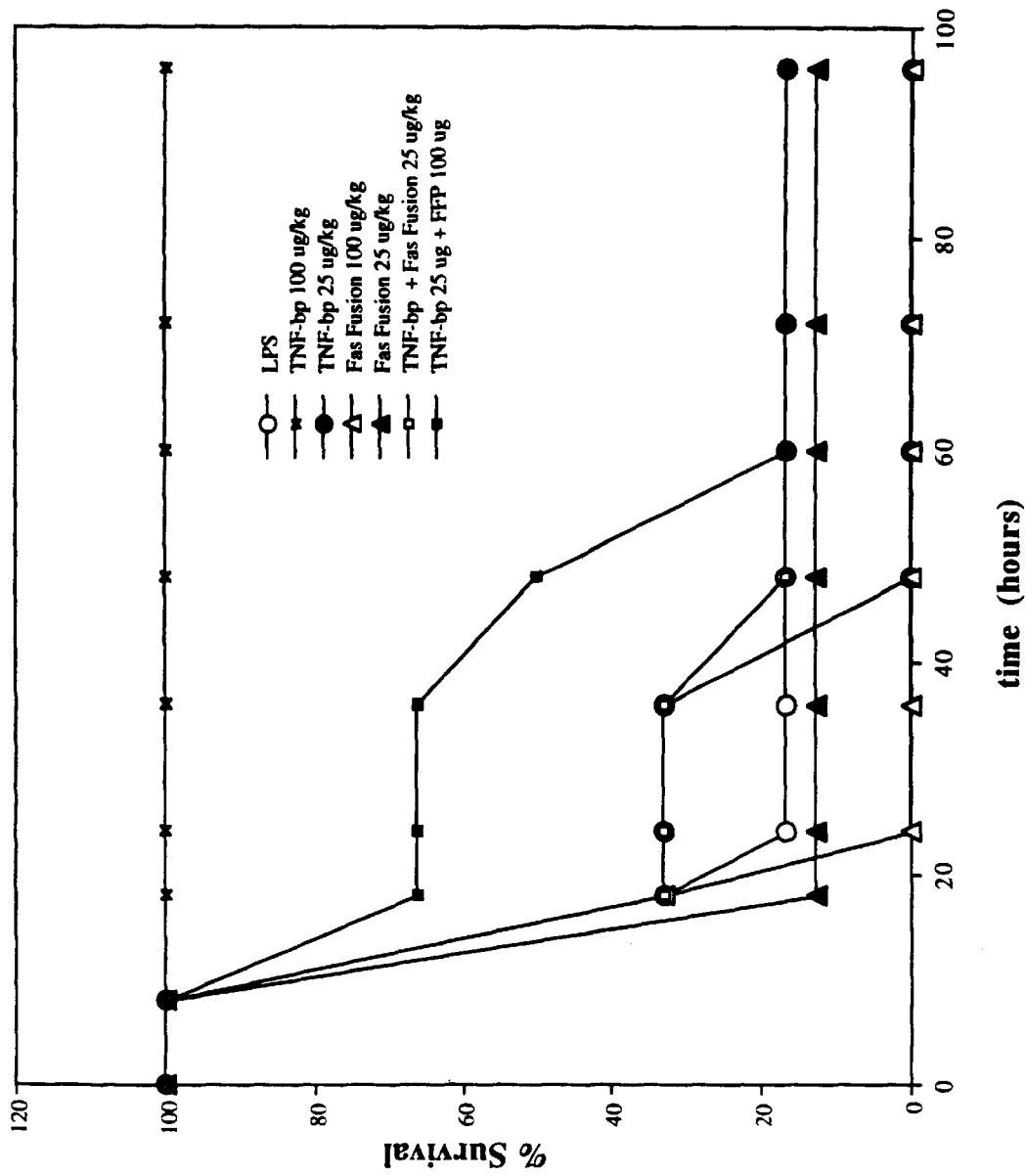
FIG. 8 depicts the effects of c105 sTNFR-I dumbbell alone, fas fusion protein alone and the combination of c105 sTNFR-I dumbbell and fas fusion protein on LPS/D-Galactosamine lethality in rats in Example 3.

As seen in FIG. 8, mice administered c105 sTNFR-I dumbbell (100 micrograms/kg; N=6; I.V.) at time=−1 hour before challenge were observed to be completely protected (100% survival) against LPS challenge in comparison to control (saline-treated) mice (N=6) challenged with LPS/ D-GalNH$_2$ (P<0.01). Mice treated with sub-optimal doses of c105 sTNFR-I dumbbell (25 micrograms/kg; N=6) were observed to have ~35% protection through +96 hours after challenge. All mice treated with fas fusion protein (100 micrograms/kg; N=6) were dead by +24 hours-post challenge. However, when mice (N=6) were treated I.V. with both c105 sTNFR-I dumbbell (25 micrograms/kg) and fas fusion protein (100 micrograms /kg), enhanced survival (70%) was observed through +36 hours in comparison to either the c105 sTNFR-I dumbbell treated (25 micrograms), fas fusion protein (100 micrograms/kg), or disease control animals alone (P<0.05). These results suggest that c105 sTNFR-I dumbbell and fas fusion protein are synergistic in their therapeutic effects in the LPS/D-GalNH$_2$ model of acute inflammation.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

We claim:

1. A pharmaceutical composition comprising a TNF binding protein and a Fas antigen.

2. The pharmaceutical composition of claim 1, wherein the Fas antigen is a fas fusion protein.

3. The pharmaceutical composition of claim 1, wherein said TNF binding protein is sTNFR-I, sTNFR-II, sTNFR fragments or sTNFR Fc.

4. The pharmaceutical composition of claim 1, wherein said TNF binding protein is present in an amount of up to about 20 mg.

5. A method for treating septic shock which comprises administering to a patient in need thereof therapeutically effective amounts of a TNF binding protein which is administered prior to, concurrently with or after administration of a Fas antigen.

6. The method of claim 5, wherein the Fas antigen is a fas fusion protein.

7. The method of claim 6, wherein said TNF binding protein and said fas fusion protein are administered in a pharmaceutically acceptable carrier.

8. The method of claim 5, wherein said TNF binding protein is sTNFR-I, sTNFR-II, sTNFR fragments or sTNFR Fc.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:

(A) LENGTH: 483 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION: 1..483

(xi) SEQUENCE DESCRIPTION: SEQ ID NO:1:

```
GAT AGT GTG TGT CCC CAA GGA AAA TAT ATC CAC CCT CAA AAT AAT TCG        48
Asp Ser Val Cys Pro Gln Gly Lys Tyr Ile His Pro Gln Asn Asn Ser
 1               5                  10                  15

ATT TGC TGT ACC AAG TGC CAC AAA GGA ACC TAC TTG TAC AAT GAC TGT        96
Ile Cys Cys Thr Lys Cys His Lys Gly Thr Tyr Leu Tyr Asn Asp Cys
                20                  25                  30

CCA GGC CCG GGG CAG GAT ACG GAC TGC AGG GAG TGT GAG AGC GGC TCC       144
Pro Gly Pro Gly Gln Asp Thr Asp Cys Arg Glu Cys Glu Ser Gly Ser
            35                  40                  45

TTC ACC GCT TCA GAA AAC CAC CTC AGA CAC TGC CTC AGC TGC TCC AAA       192
Phe Thr Ala Ser Glu Asn His Leu Arg His Cys Leu Ser Cys Ser Lys
 50                  55                  60

TGC CGA AAG GAA ATG GGT CAG GTG GAG ATC TCT TCT TGC ACA GTG GAC       240
Cys Arg Lys Glu Met Gly Gln Val Glu Ile Ser Ser Cys Thr Val Asp
 65                  70                  75                  80

CGG GAC ACC GTG TGT GGC TGC AGG AAG AAC CAG TAC CGG CAT TAT TGG       288
Arg Asp Thr Val Cys Gly Cys Arg Lys Asn Gln Tyr Arg His Tyr Trp
                85                  90                  95

AGT GAA AAC CTT TTC CAG TGC TTC AAT TGC AGC CTC TGC CTC AAT GGG       336
Ser Glu Asn Leu Phe Gln Cys Phe Asn Cys Ser Leu Cys Leu Asn Gly
            100                 105                 110

ACC GTG CAC CTC TCC TGC CAG GAG AAA CAG AAC ACC GTG TGC ACC TGC       384
Thr Val His Leu Ser Cys Gln Glu Lys Gln Asn Thr Val Cys Thr Cys
        115                 120                 125

CAT GCA GGT TTC TTT CTA AGA GAA AAC GAG TGT GTC TCC TGT AGT AAC       432
His Ala Gly Phe Phe Leu Arg Glu Asn Glu Cys Val Ser Cys Ser Asn
130                 135                 140

TGT AAG AAA AGC CTG GAG TGC ACG AAG TTG TGC CTA CCC CAG ATT GAG       480
Cys Lys Lys Ser Leu Glu Cys Thr Lys Leu Cys Leu Pro Gln Ile Glu
145                 150                 155                 160

AAT                                                                   483
Asn
```

(2) INFORMATION FOR SEQ ID NO:2:

(i) SEQUENCE CHARACTERISTICS:
        (A) LENGTH: 161 amino acids
        (B) TYPE: amino acid
        (D) TOPOLOGY: linear (ii) MOLECULE TYPE: protein (xi) SEQUENCE DESCRIPTION: SEQ ID NO:2:

```
Asp Ser Val Cys Pro Gln Gly Lys Tyr Ile His Pro Gln Asn Asn Ser
 1               5                  10                  15

Ile Cys Cys Thr Lys Cys His Lys Gly Thr Tyr Leu Tyr Asn Asp Cys
                20                  25                  30

Pro Gly Pro Gly Gln Asp Thr Asp Cys Arg Glu Cys Glu Ser Gly Ser
            35                  40                  45

Phe Thr Ala Ser Glu Asn His Leu Arg His Cys Leu Ser Cys Ser Lys
 50                  55                  60
```

```
Cys Arg Lys Glu Met Gly Gln Val Glu Ile Ser Ser Cys Thr Val Asp
 65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn
```

(2) INFORMATION FOR SEQ ID NO:3:

(i) SEQUENCE CHARACTERISTICS:
        (A) LENGTH: 705 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION: 1..705

(xi) SEQUENCE DESCRIPTION: SEQ ID NO:3:

```
TTG CCC GCC CAG GTG GCA TTT ACA CCC TAC GCC CCG GAG CCC GGG AGC    48
Leu Pro Ala Gln Val Ala Phe Thr Pro Tyr Ala Pro Glu Pro Gly Ser
 1               5                  10                  15

ACA TGC CGG CTC AGA GAA TAC TAT GAC CAG ACA GCT CAG ATG TGC TGC    96
Thr Cys Arg Leu Arg Glu Tyr Tyr Asp Gln Thr Ala Gln Met Cys Cys
                 20                  25                  30

AGC AAG TGC TCG CCG GGC CAA CAT GCA AAA GTC TTC TGT ACC AAG ACC   144
Ser Lys Cys Ser Pro Gly Gln His Ala Lys Val Phe Cys Thr Lys Thr
             35                  40                  45

TCG GAC ACC GTG TGT GAC TCC TGT GAG GAC AGC ACA TAC ACC CAG CTC   192
Ser Asp Thr Val Cys Asp Ser Cys Glu Asp Ser Thr Tyr Thr Gln Leu
 50                  55                  60

TGG AAC TGG GTT CCC GAG TGC TTG AGC TGT GGC TCC CGC TGT AGC TCT   240
Trp Asn Trp Val Pro Glu Cys Leu Ser Cys Gly Ser Arg Cys Ser Ser
 65                  70                  75                  80

GAC CAG GTG GAA ACT CAA GCC TGC ACT CGG GAA CAG AAC CGC ATC TGC   288
Asp Gln Val Glu Thr Gln Ala Cys Thr Arg Glu Gln Asn Arg Ile Cys
                 85                  90                  95

ACC TGC AGG CCC GGC TGG TAC TGC GCG CTG AGC AAG CAG GAG GGG TGC   336
Thr Cys Arg Pro Gly Trp Tyr Cys Ala Leu Ser Lys Gln Glu Gly Cys
             100                 105                 110

CGG CTG TGC GCG CCG CTG CGC AAG TGC CGC CCG GGC TTC GGC GTG GCC   384
Arg Leu Cys Ala Pro Leu Arg Lys Cys Arg Pro Gly Phe Gly Val Ala
         115                 120                 125

AGA CCA GGA ACT GAA ACA TCA GAC GTG GTG TGC AAG CCC TGT GCC CCG   432
Arg Pro Gly Thr Glu Thr Ser Asp Val Val Cys Lys Pro Cys Ala Pro
130                 135                 140

GGG ACG TTC TCC AAC ACG ACT TCA TCC ACG GAT ATT TGC AGG CCC CAC   480
Gly Thr Phe Ser Asn Thr Thr Ser Ser Thr Asp Ile Cys Arg Pro His
145                 150                 155                 160

CAG ATC TGT AAC GTG GTG GCC ATC CCT GGG AAT GCA AGC AGG GAT GCA   528
```

```
Gln Ile Cys Asn Val Val Ala Ile Pro Gly Asn Ala Ser Arg Asp Ala
                165                 170                 175

GTC TGC ACG TCC ACG TCC CCC ACC CGG AGT ATG GCC CCA GGG GCA GTA      576
Val Cys Thr Ser Thr Ser Pro Thr Arg Ser Met Ala Pro Gly Ala Val
        180                 185                 190

CAC TTA CCC CAG CCA GTG TCC ACA CGA TCC CAA CAC ACG CAG CCA ACT      624
His Leu Pro Gln Pro Val Ser Thr Arg Ser Gln His Thr Gln Pro Thr
        195                 200                 205

CCA GAA CCC AGC ACT GCT CCA AGC ACC TCC TTC CTG CTC CCA ATG GGC      672
Pro Glu Pro Ser Thr Ala Pro Ser Thr Ser Phe Leu Leu Pro Met Gly
        210                 215                 220

CCC AGC CCC CCA GCT GAA GGG AGC ACT GGC GAC                          705
Pro Ser Pro Pro Ala Glu Gly Ser Thr Gly Asp
225                 230                 235
```

(2) INFORMATION FOR SEQ ID NO:4:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO:4:

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Arg Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```